US008262565B2

(12) United States Patent
Okada

(10) Patent No.: US 8,262,565 B2
(45) Date of Patent: Sep. 11, 2012

(54) ENDOSCOPE SYSTEM

(75) Inventor: Tsutomu Okada, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1227 days.

(21) Appl. No.: 11/698,522

(22) Filed: Jan. 26, 2007

(65) Prior Publication Data

US 2007/0179341 A1   Aug. 2, 2007

(30) Foreign Application Priority Data

Jan. 31, 2006  (JP) ................................ P2006-021961

(51) Int. Cl.
*A61B 1/00* (2006.01)
*A61B 1/12* (2006.01)

(52) U.S. Cl. ........ 600/156; 600/104; 600/153; 600/154; 600/158; 600/159; 600/562; 600/565; 600/571; 600/573; 606/113; 606/114; 606/115

(58) Field of Classification Search .................. 600/104, 600/153, 154, 156–159, 562, 565, 571, 573; 606/113–115; 604/317, 319–326
See application file for complete search history.

(56) References Cited

U.S. PATENT DOCUMENTS

| | | | | |
|---|---|---|---|---|
| 4,469,090 A * | 9/1984 | Konomura | ..................... | 600/159 |
| 4,957,492 A * | 9/1990 | McVay | .......................... | 604/319 |
| 5,035,688 A * | 7/1991 | Inui | ................................ | 604/190 |
| 5,363,860 A * | 11/1994 | Nakao et al. | .................. | 600/573 |
| 5,456,689 A | 10/1995 | Kresch et al. | | |
| 5,624,418 A | 4/1997 | Shepard | | |
| 5,971,917 A * | 10/1999 | Komi et al. | ..................... | 600/159 |
| 6,110,127 A * | 8/2000 | Suzuki | .......................... | 600/565 |
| 6,142,956 A * | 11/2000 | Kortenbach et al. | .......... | 600/564 |
| 6,428,316 B1 * | 8/2002 | Rodriquez | ....................... | 433/92 |
| 7,244,236 B2 * | 7/2007 | Merkle | ......................... | 600/575 |

(Continued)

FOREIGN PATENT DOCUMENTS

EP   1 736 103 A1   12/2006

(Continued)

OTHER PUBLICATIONS

Japanese Office Action dated May 17, 2011 from corresponding Japanese Application No. 2006-021961 with English language translation.

(Continued)

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

In the endoscope system 1, a tissue recovery device 3 that recovers tissue is directly mounted on an endoscope 2. The tissue recovery device 3 has a filter portion, and the filter portion is inserted so as to traverse the conduit of the suction conduit 20 that passes inside the endoscope operation portion 10. The suction conduit 20 opens to the distal end portion of the endoscope insertion portion 11, and the working channel 23 branches off from the branch portion 22 that is provided further on the distal end side than the insertion location of the tissue recovery device 3. With this endoscope system, it is possible to reduce operational burden of the operator with regard to the endoscope system that includes the tissue recovery device that recovers tissue.

9 Claims, 16 Drawing Sheets

U.S. PATENT DOCUMENTS

| | | | |
|---|---|---|---|
| 8,070,756 B2 * | 12/2011 | Secrest et al. | 606/113 |
| 8,088,079 B2 * | 1/2012 | Kaye et al. | 600/562 |
| 2004/0068291 A1 * | 4/2004 | Suzuki | 606/205 |
| 2005/0119522 A1 * | 6/2005 | Okada | 600/106 |

FOREIGN PATENT DOCUMENTS

| | | |
|---|---|---|
| EP | 1 774 896 A1 | 4/2007 |
| JP | 62-74804 | 5/1987 |
| JP | 6-304129 | 11/1994 |
| JP | 7-184847 | 7/1995 |
| JP | H8-299255 | 11/1996 |
| JP | 11-267089 | 10/1999 |
| JP | 2000-237126 A | 9/2000 |
| JP | 2000-287985 | 10/2000 |
| JP | 2005-211453 | 8/2005 |
| JP | 2007-029194 A | 2/2007 |
| WO | WO 2004/075740 A1 | 9/2004 |

OTHER PUBLICATIONS

Japanese Office Action dated Oct. 18, 2011 from corresponding Japanese Patent Application No. 2006-021961 together with a partial English language translation.

* cited by examiner

ENDOSCOPE SYSTEM

BACKGROUND OF THE INVENTION

1. Field of the Invention

The present invention relates to an endoscope system that is used in through-endoscope treatment and can recover tissue sampled from a living body.

Priority is claimed on Japanese Patent Application No. 2006-021961, filed Jan. 31, 2006, the content of which is incorporated herein by reference.

2. Description of Related Art

As a method of recovering extracted living body tissue, there has conventionally been a method of suctioning tissue that is resected by a treatment tool using a channel of an endoscope. For example, there is one that constitutes a tissue recovery trap by forming a sealable chamber with a cap on the forceps opening of the forceps channel of the endoscope and disposing a net in this chamber (refer to Japanese Examined Utility Model Application, First Publication No. S62-74804). On the inner side of this net, there is inserted a pipe that constitutes a suction channel while serving as the forceps channel, and on the outer side of this net there is disposed a pipe that is connected to a suction unit. By operating the suction unit, the tissue that is resected or the like in the body is drawn through the pipe to be led to the net. The net is of a shape through which fluid can pass but tissue cannot pass, and so only tissue is caught by the net.

There is also one in which a suction tube that is connected to the proximal end portion of a forceps channel of an endoscope is drawn to outside the endoscope and, after providing a valve and a recovery trap in the middle of this suction tube, providing a connection to a suction unit (refer to Japanese Unexamined Patent Application, First Publication No. H11-267089). When tissue such as a polyp is resected by resection forceps through the forceps channel, the resection forceps are extracted from the forceps channel, whereby the forceps opening is closed by a forceps plug. When the valve is opened, the suction force by the suction unit acts on the forceps channel through the suction tube, whereby the tissue is suctioned. The tissue then enters the suction tube from the forceps channel and passes through the outside of the endoscope to be recovered in the recovery trap.

SUMMARY OF THE INVENTION

The invention according to the present invention is an endoscope system that includes an endoscope in which an endoscope insertion portion that is inserted into a body extends from an endoscope operation portion that an operator controls; a suction conduit that opens to a distal end portion of the endoscope insertion portion and passes through the endoscope, with its proximal end portion connected to a suction unit; a working channel that branches off and extends from a branch portion that is formed in the suction conduit and allows the insertion of a treatment tool toward the opening of the distal end portion of the suction conduit; and a tissue recovery device that is provided in the endoscope operating portion further to the proximal end side than the branch portion of the suction conduit and capable of trapping tissue that is suctioned by the suction conduit.

The other invention according to the present invention is an endoscope system that includes an endoscope in which an endoscope insertion portion that is inserted into a body extends from an endoscope operation portion that an operator controls; a working channel that opens to a distal end portion of the endoscope insertion portion, passes through the endoscope to have its proximal end portion open to the endoscope operation portion; a tissue recovery device that is connected to a connection conduit that branches from a branch portion formed at the proximal end side of the working channel and is capable of trapping tissue that is drawn into the working channel; and a suction conduit for suctioning tissue via the tissue recovery device and the working channel, being connected to the tissue recovery device and connected to a suction unit through the inside of the endoscope.

Preferably the endoscope system has an attachment in which a portion of the working channel that includes the branch portion and the distal end portion of the suction conduit that is connected to the tissue recovery device are formed to be removably attached as one piece with respect to the endoscope operation portion.

Preferably the tissue recovery device in the endoscope system is removably attached to the attachment.

Preferably the attachment in the endoscope system is manufactured from an elastic member.

Preferably the attachment in the endoscope system has a bypass conduit that bypasses the tissue recovery device to allow communication between the connection conduit and the suction conduit, with the bypass conduit being blocked when the tissue recovery device is attached and opened when the tissue recovery device is removed.

Preferably the tissue recovery device in the endoscope system has a tissue recovery case and a tissue recovery filter that is removably attached to the tissue recovery case.

Preferably the attachment in the endoscope system has a main body portion that is attached to and detached from the endoscope and a valve that is inserted in the main body to rotate freely, with the valve being rotated so as to be able to select a first rotation position that allows communication between the distal end portion of the suction conduit and the proximal end portion of the working channel via the bypass conduit, and a second rotation position that blocks the bypass conduit to separately open the distal end portion of the suction conduit and the proximal end portion of the working channel to the outside.

Preferably the tissue recovery filter in the endoscope system consists of two tissue trapping surfaces provided back to back, and the tissue recovery case being constituted so as to mount the tissue recovery filter so that the tissue trapping surfaces are disposed approximately perpendicular to the flow path of a fluid that suctions tissue.

Preferably the endoscope system is further provided with a coupling member that is mountable on a distal end side connection port that is provided on the proximal end of the connection conduit of the attachment to be connectable with the tissue recovery device and a proximal end side connection port that is provided on the conduit forming the distal end portion of the suction conduit in the attachment to be connectable with the tissue recovery device to thereby fluidly connect the working channel and the suction conduit.

Preferably the endoscope system is provided with a first plug body that is mountable in the distal end side connection port of the connection conduit that is open to the outside when the tissue recovery device is removed from the attachment, and a second plug body that is mountable in the distal end side connection port of the connection conduit that is open to the outside when the tissue recovery device is removed from the attachment.

Preferably the attachment in the endoscope system has a first face that faces the endoscope operation portion when mounted on the endoscope operation portion and being constituted so that the tissue recovery device is disposed on a second face that is on the opposite side of the first face.

Preferably the tissue recovery device in the endoscope system is removably attached to the suction conduit.

DETAILED DESCRIPTION OF THE INVENTION

Embodiments of the present invention will be explained in detail below, referring to the attached drawings.

First Embodiment

Figure 1:
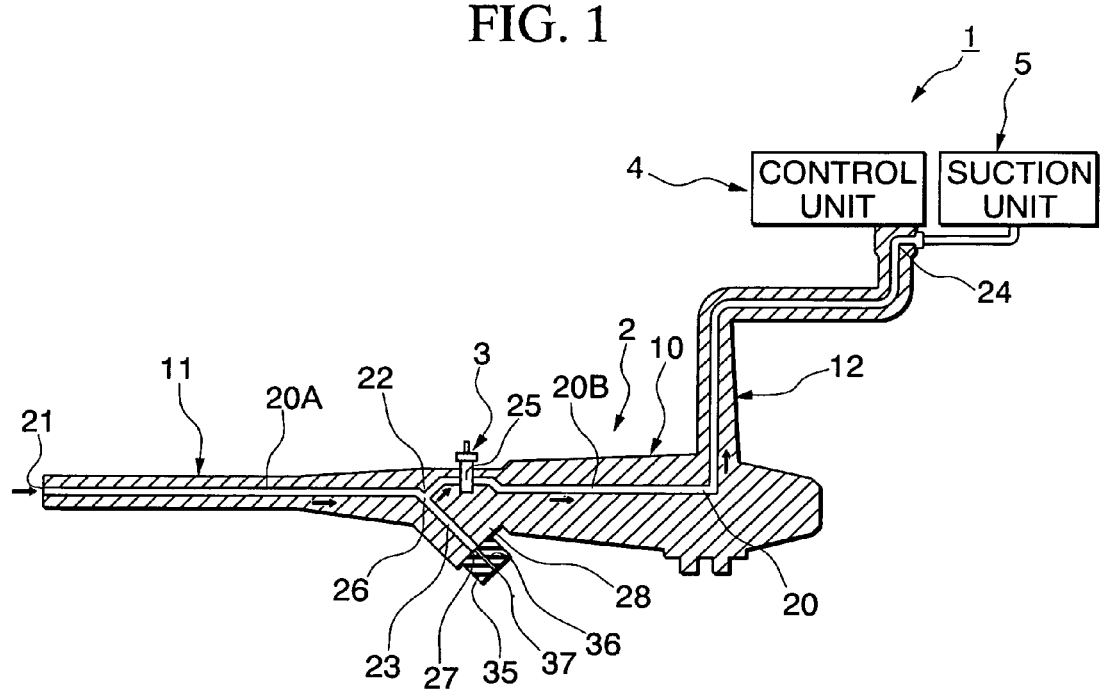
FIG. 1 is a drawing showing an outline configuration of the endoscope system according to an embodiment of the present invention.

FIG. 1 shows the outline configuration of the endoscope system according to the present embodiment. In the drawing, an endoscope system 1 is provided with an endoscope 2, a tissue recovery device 3 that is mounted in the endoscope 2, a control unit 4 of the endoscope 2, and a suction unit 5.

The endoscope 2 has an endoscope operation portion 10 that an operator controls and an elongated endoscope insertion portion 11 that extends from the distal end of the endoscope operation portion 10 and has flexibility. An angle knob and various buttons and switches are arranged on the endoscope operation portion 10, and it is connected to a control unit 4 via a universal cable 12. A suction conduit 20 is formed inside the endoscope 2. The suction conduit 20 has a distal end opening portion 21 at the distal end portion of the endoscope insertion portion 11 and consists of a first conduit portion 20A that extends into the endoscope operation portion 10, a branch portion 22 that is provided at the proximal end of a first conduit portion 20A, and a second conduit portion 20B that is drawn from the branch portion 22 to the universal cable 12 through the endoscope operation portion 10. A proximal end portion 24 of the second conduit portion 20B is connected to the suction unit 5. It is also possible to provide other conduits in the endoscope 2 that are not illustrated.

Figure 2:
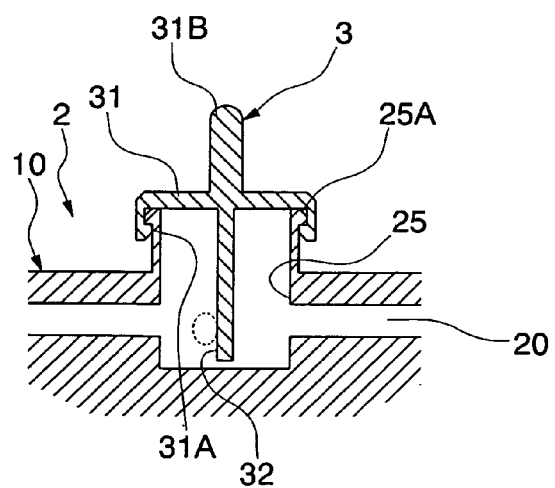
FIG. 2 is a partially enlarged cross section of FIG. 1, showing the outline configuration of the tissue recovery device.

In the endoscope operation portion 10, a recovery mounting portion 25 is provided in a depressed manner in the second conduit portion 20B which is further to the proximal end side than the branch portion 22 of the suction conduit 20. The opening portion of the recovery mounting portion 25 projects to the outside from the periphery of the endoscope operation portion 10 in the diameter direction, and a flange 25A is annularly formed on the periphery of the opening portion. As shown in FIG. 2, the tissue recovery device 3 is detachably mounted in the recovery mounting portion 25 so as to seal the opening portion. The tissue recovery device 3 has a lid 31 that seals the opening portion of the recovery mounting portion 25. A flange 31A that latches with the flange 25A of the recovery mounting portion 25 and a knob 31B that the operator grasps are formed on the lid 31. A filter portion 32 is provided in an extending manner on the inner surface side of the lid 31. The filter portion 32 has a mesh structure and traverses the suction conduit 20. The mesh is formed so that numerous holes are parallel to the suction conduit 20, with the front surface facing the suction conduit 20 and the reverse surface with respect to the front surface serving as tissue trapping surfaces. The gap between the recovery mounting portion 25 and the filter portion 32 is of a size through which tissue cannot pass.

A distal end side opening portion 26 of the working channel 23 is coupled to the branch portion 22 of the suction conduit 20. The proximal end side connection port 27 of the working channel 23 is formed on the side portion 28 of the endoscope operation portion 10. A plug 35 is mounted in the proximal end side connection port 27. A hole 36 that can communicate with the working channel 23 is formed in the plug 35, and this hole 36 forms a treatment tool insertion port 37. The plug 35 is, for example, made from an elastic member, and the hole 36 is sealed in the state of a treatment tool not inserted. The working channel 23 is connected to the branch portion 22 of the suction pipe 20 so that when a treatment tool is to be inserted, the treatment tool is inserted in the first conduit portion 20A of the suction conduit 20 and the treatment tool projects from the distal end opening portion 21 of the suction conduit 20.

Next, the action of the present embodiment will be described.

First, the endoscope insertion portion 11 is inserted from a mouth of the patient, and guided to the location where tissue is to be sampled. When resecting tissue, the treatment tool (for example, resection forceps, snare, and the like) is inserted from the treatment tool insertion port 37. The treatment tool is inserted from the treatment tool insertion port 37 of the plug 35 into the proximal end side connection port 27 of the working channel 23 and, following the shape of the branch portion 22, is guided from the distal end side opening portion 26 to the distal end side of the suction conduit 20. Furthermore, it proceeds in the endoscope insertion portion 11 along the suction conduit 20 to protrude from the distal end opening portion 21. When the treatment tool consists of resection forceps, the tissue that is the sample object is resected by opening and closing the pair of forceps that are provided at the distal end. When the resection is finished, the resection forceps are withdrawn from the endoscope 2. The treatment tool, passing through the branch portion 22 from the suction conduit 20, is pulled out from the working channel 23. The treatment tool insertion port 37 of the plug 35 is closed up by its own restoring force.

When recovering tissue, the suction unit 5 is operated. The tissue recovery device 3 and the suction conduit 20 are maintained in an air-tight condition, and on the working channel 23 side thereof, air-tightness is maintained by the plug 35. Therefore, a suction force acts at the distal end opening portion 21 of the suction conduit 20, as shown by the arrow in FIG. 1, so that the resected tissue is drawn into the suction conduit 20. In the suction conduit 20, the tissue is guided to the recovery mounting portion 25 through the branch portion 22 as shown by the arrow. The tissue recovery device 3 is mounted at the recovery mounting portion 25, with the mesh structure of the filter portion 32 passing fluid but not allowing tissue to pass. Tissue therefore becomes caught on the filter portion 32 as shown by the imaginary line in FIG. 2. After the suction unit 5 is stopped, by removing the tissue recovery device 3 from the recovery mounting portion 25, the tissue that is caught on the filter portion 32 is recovered.

The present embodiment has a constitution in which the tissue recovery device 3 is directly mounted on the endoscope 2 side. Therefore, the number of pipes extending from the endoscope operating portion 10 to the outside can be reduced. Moreover, since the tissue recovery device 3 is fixed to the endoscope 2, handling of the tissue recovery device 3 becomes easy. The burden on the operator can thus be reduced, enabling a procedure to be quickly carried out. Moreover, the tissue recovery device 3 is provided in the conduit (further to the proximal end portion side than the branch portion 22 of the suction conduit 20) that branches off from the working channel 23, which is the conduit through which the treatment tool is pulled or inserted, therefore simplifying removal and insertion of the treatment tool.

Second Embodiment

A second embodiment of the present invention will be described, referring to FIG. 3 to FIG. 23. Constituent elements similar to those in the first embodiment will be given the same reference numerals and explanations thereof will be omitted here.

Figure 3:
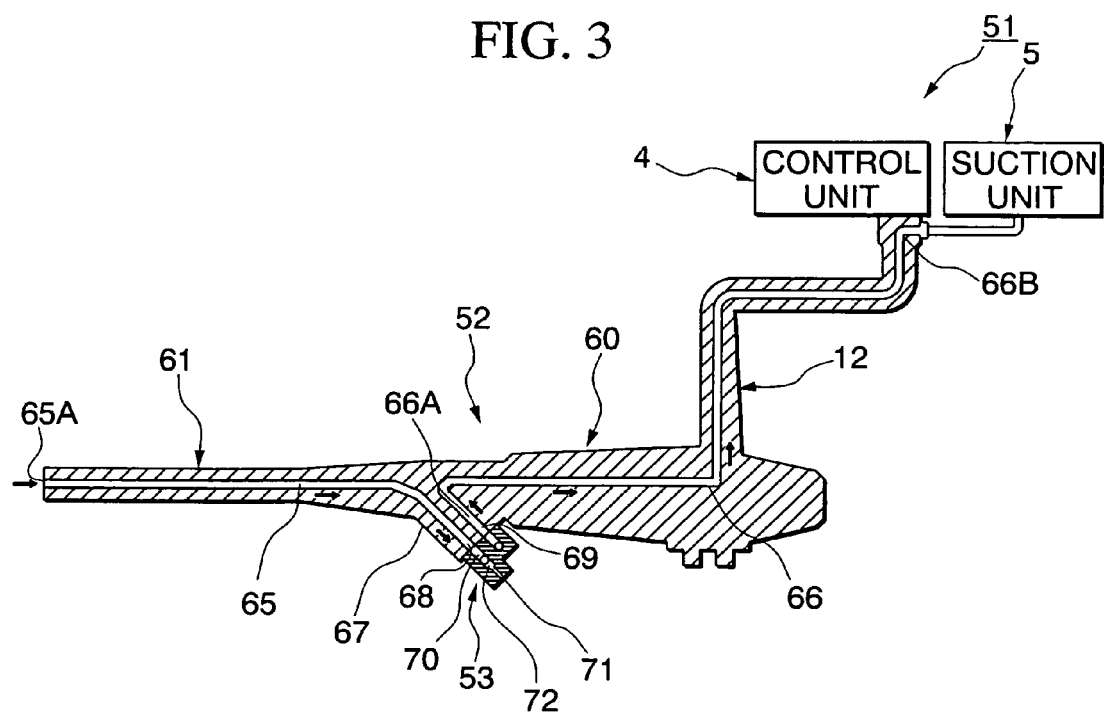
FIG. 3 is a drawing showing an outline configuration of the endoscope system.
Figure 4:
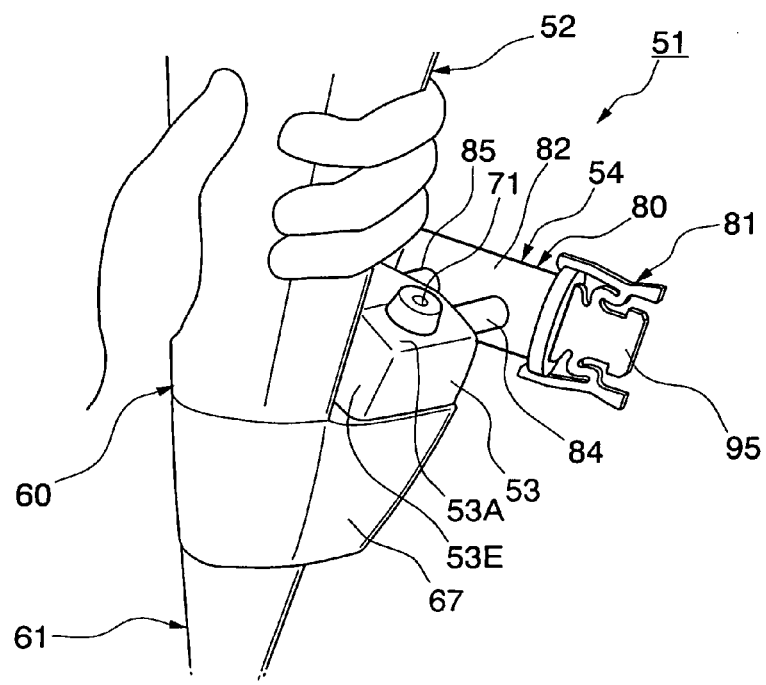
FIG. 4 is a drawing showing the state of the tissue recovery device mounted on the endoscope via the attachment.

As shown in FIG. 3 and FIG. 4, an endoscope system 51 is provided with an endoscope 52, a control unit 4, a suction unit 5, an attachment 53 that is removably attached to the endoscope 52, and a tissue recovery device 54 that is fixed to the endoscope 52 via the attachment 53.

The endoscope 52 has an endoscope operation portion 60 and an endoscope insertion portion 61 which differ from the first embodiment only in the constitution of the conduit. In the endoscope 52, a working channel 65 and a suction conduit 66 are formed. The working channel 65 has a distal end opening portion 65A at the distal end portion of the endoscope insertion portion 61, and extends until a side portion 67 of the endoscope operation portion 60. A proximal end side connection port of the working channel 65 protrudes from the side portion 67 to form a first connection portion 68. A distal end portion 66A of the suction conduit 66 also opens to the side portion 67. This opening is formed at a second connection portion 69 that projects from the side portion 67. The suction conduit 66 passes from the endoscope operation portion 60 through a universal cable 12, and a proximal end portion 66B thereof is connected to the suction unit 5. The first connection portion 68 and the second connection portion 69 project from the side portion 67 in an approximately parallel manner.

Figure 5:
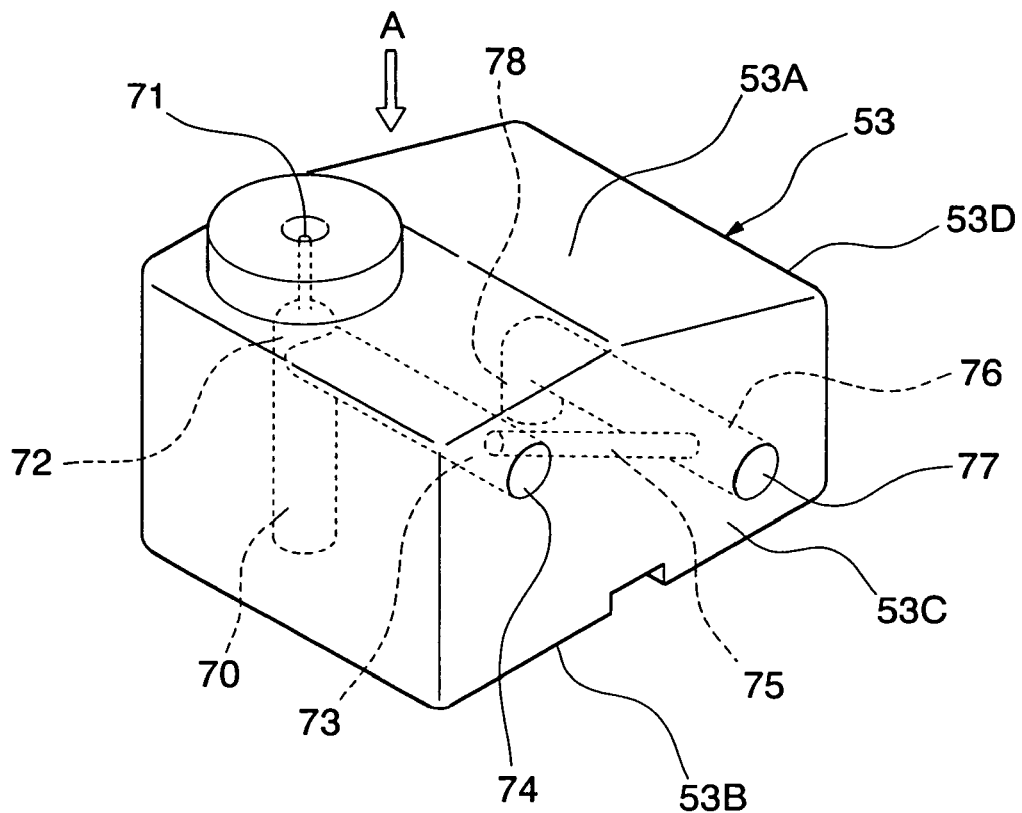
FIG. 5 is a perspective view of the attachment.
Figure 6:
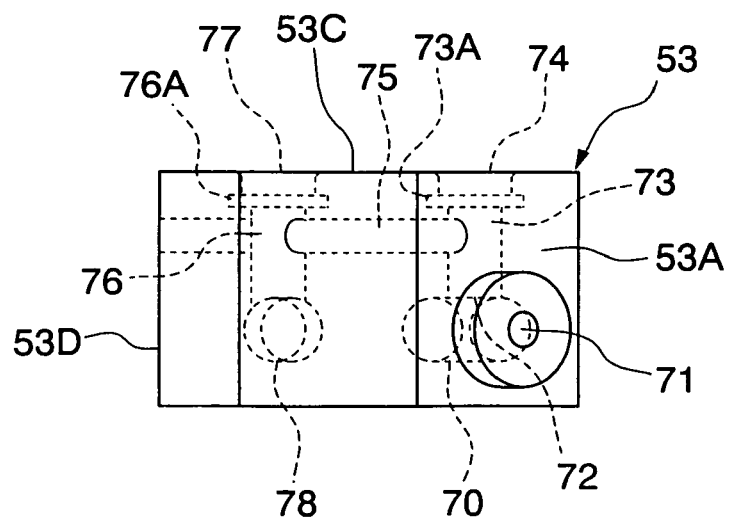
FIG. 6 is a view from the arrow A in FIG. 5.

The attachment 53 is mounted on the first connection portion 68 and the second connection portion 69. The attachment 53 is, for example, made from a material with a hardness and strength that are low compared to the endoscope 52 side, such as a plastic or an elastic material or the like. As shown in FIGS. 4 to 6, the attachment 53 is formed so that a first coupling conduit 70 that forms a portion of the working channel 65 penetrates from a top surface 53A to a bottom surface 53B of the attachment 53. The first coupling conduit 70 has a shape that can fit the first connection portion 68 on the bottom surface 53B side. A treatment tool insertion port 71 is formed on the top surface 53A side of the first coupling conduit 70. Moreover, a branch portion 72 is formed in the first coupling conduit 70, and a first connection conduit 73 extends therefrom. The first connection conduit 73 opens to a side surface 53C of the attachment 53, and this opening portion serves as a distal end side connection port 74. In the first connection conduit 73, a bypass conduit 75 is connected. The bypass conduit 75 passes through a second connection conduit 76 to open at a side surface 53D of the attachment 53. The bypass conduit 75, when the bottom surface 53B of the attachment 53 is disposed facing down, has a slope so that the first connection conduit 73 side is relatively higher than the second connection conduit 76 side. The diameter of the bypass conduit is smaller than the diameter of the first connection conduit 73 and the second connection conduit 76.

The second connection conduit 76 extends almost parallel with the first connection conduit 73, and one end portion forms a proximal end side connection port 77 on the side surface 53C of the attachment 53. The other end portion connects to a second coupling conduit 78 in the attachment 53. The second coupling conduit 78 has an opening portion only on the bottom surface 53B of the attachment 53. This opening portion has a shape that can fit the second connection portion 69 on the endoscope 52 side.

The tissue recovery device 54 is detachably mounted on the distal end side connection port 74 and the proximal end side connection port 77 of the attachment 53. As shown in FIG. 4 and FIGS. 7 to 9, the tissue recovery device 54 consists of a tissue recovery case 80 and a tissue recovery filter 81 that is detachably mounted on the tissue recovery case 80. The tissue recovery case 80 has a bottomed, cylindrical case body 82 that is made from a material that allows confirmation of the content by visual inspection. On a side portion of the case body 82, a distal end side conduit 84 and a proximal end side conduit 85 extend in turn from the side of an opening portion 83 at an angle to the case body 82 and parallel to each other. An annular projection 84A and an annular projection 84B with a larger diameter than the annular projection 84A are provided in a protruding manner on the outer circumference of the distal end side conduit 84. An annular projection 85A and an annular projection 85B with a larger diameter than the annular projection 85A are provided in a protruding manner on the outer circumference of the proximal end side conduit 85. These conduits 84 and 85 are in communication with each other inside the case body 82.

Figure 9:
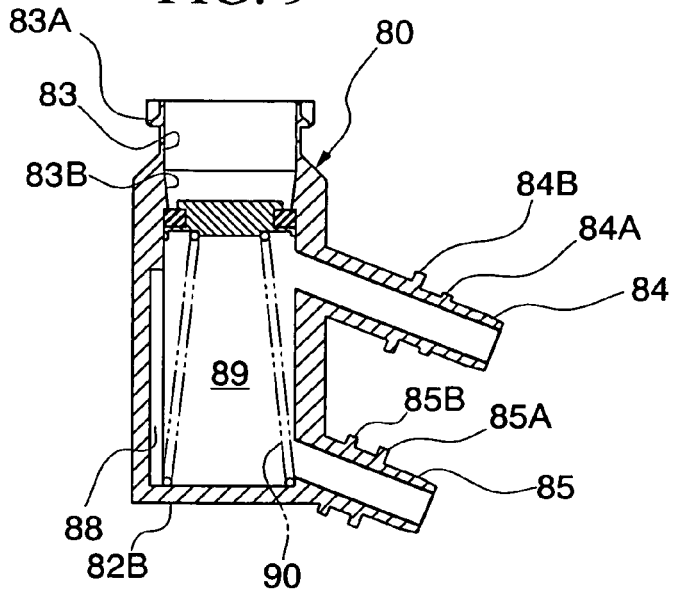
FIG. 9 is a sectional view showing the tissue recovery case when the tissue recovery filter is removed.

The case body 82 has the round opening portion 83 and a pair of locking projections 83A are provided on the outer circumference of the opening portion 83. The locking projections 83A are disposed on the same diameter of the opening portion 83. On the inside of the opening portion 83 of the case body 82 is provided a tapered surface 83B whose diameter contracts toward a bottom portion 82B of the case body. A lid 86 is inserted more toward the bottom portion 82B side than the opening portion 83 of the case body 82. The lid 86 is slidable in the longwise direction of the case body 82 while maintaining airtightness with the inner wall of the case body 82 by means of a sealing member 87. Here, on the inner circumference side of the case body 82, a groove 88 for communication is formed along the lengthwise direction. When the lid 86 is located midway in this groove 88, a space 89A from the top surface of the lid 86 to the opening portion 83 of the case body 82 and a space 89B from the bottom surface of the lid 86 to the bottom portion 82B of the case body 82 can be brought into communication. The groove 88 extends from the bottom portion 82B to the connection position of the distal end side conduit 84. A coil spring 90 is inserted as a biasing means between the lid 86 and the bottom portion 82B of the case body 82. The lid 86 is thus biased toward the opening portion 83. As shown in FIG. 9, in a no-load state, the lid 86 abuts a step portion 91 that is formed by the tapered surface 83B, and so can go no further outside. In this position, the inside of the case body 82 is continuous with the distal end side conduit 84 and the proximal end side conduit 85, and the opening portion 83 is sealed by the lid 86.

Figure 7:
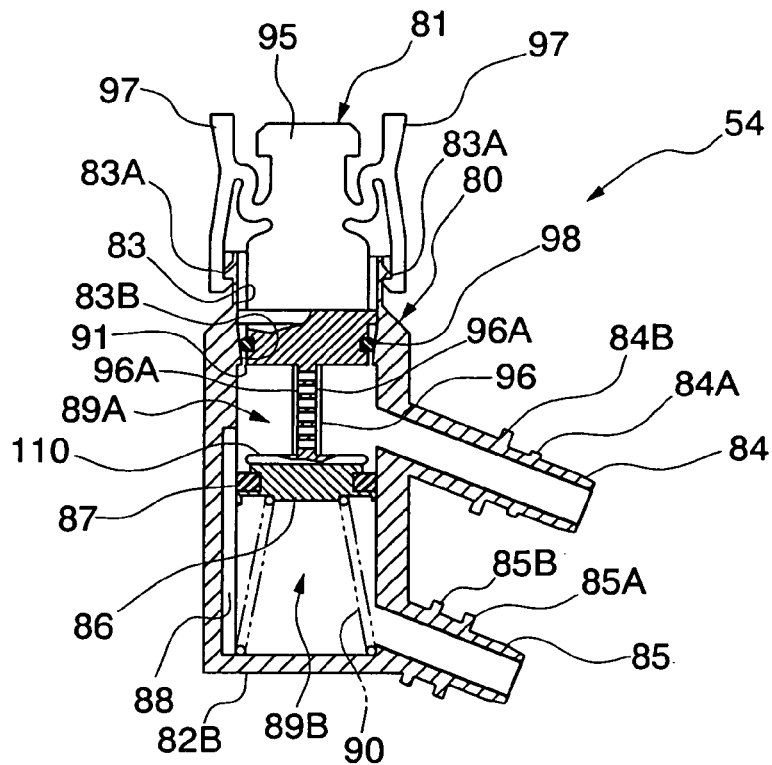
FIG. 7 is a sectional drawing showing the constitution of the tissue recovery device.
Figure 8:
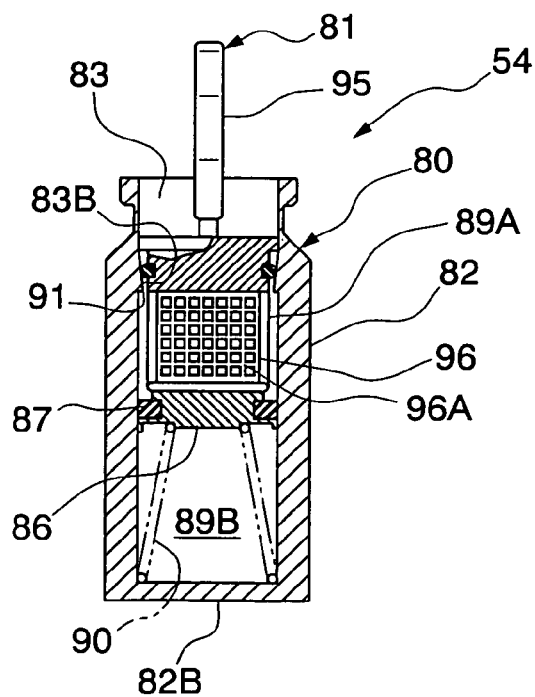
FIG. 8 is a sectional view of the tissue recovery device.
Figure 10:
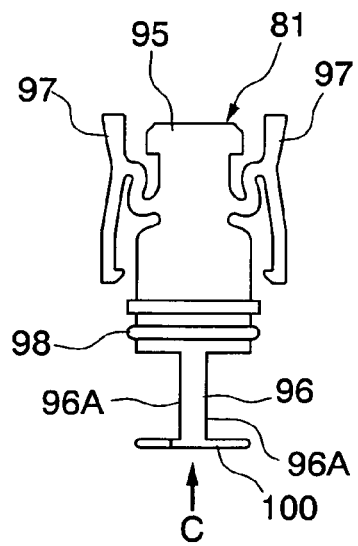
FIG. 10 is a drawing showing the constitution of the tissue recovery filter.

As shown in FIG. 7, FIG. 8 and FIG. 10, the tissue recovery filter 81 has a lid portion 95 that is insertable in the opening portion 83 of the case body 82, with a filter portion 96 provided in an extending manner from the lid portion 95.

A pair of fixing portions 97 are provided in the lid portion 95. The fixing portions 97 can clickably engage with the locking projections 83A of the case body 82. Also, an O-ring 98 that serves as a sealing member is mounted on the lid portion 95, and by being crushed by the tapered surface 83B, hermetically seals the opening portion 83 of the case body 82. The filter portion 96 has a mesh shape through which fluids can pass but tissue is caught. The filter portion 96 consists of two tissue trapping surfaces 96A provided back to back. The tissue trapping surfaces 96A are perpendicularly disposed with respect to a line segment connecting the fixing portions 97. Accordingly, by locking the fixing portions 97 onto the locking projections 83A on the case body 82 side, one of the tissue catching surfaces 96A is disposed facing the distal end side conduit 84. Therefore, it is possible to attach the tissue recovery filter 81 without regard to orientation. The gap between the filter portion 96 and the case body 82 is of a size that does not allow tissue to pass.

Figure 11:
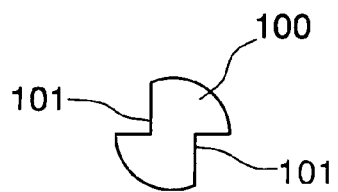
FIG. 11 is a drawing from the arrow C in FIG. 10 showing the shape of a plate.

A plate 100 is provided at the distal end of the filter portion 96. As shown in FIG. 11, notches 101 are provided in this plate 100, so that when removing the tissue recovery filter 81, fluid in the case body 82 is not scooped out. As shown in FIG. 7, when the tissue recovery filter 81 is mounted in the tissue recovery case 80, the plate 100 on the distal end of the filter portion 96 pushes the lid 86 to the bottom portion side 82B. The filter portion 96 pushes the lid 86 against the coil spring 90 so as to be in a position between the distal end side conduit 84 and the proximal end side conduit 85.

Figure 12:
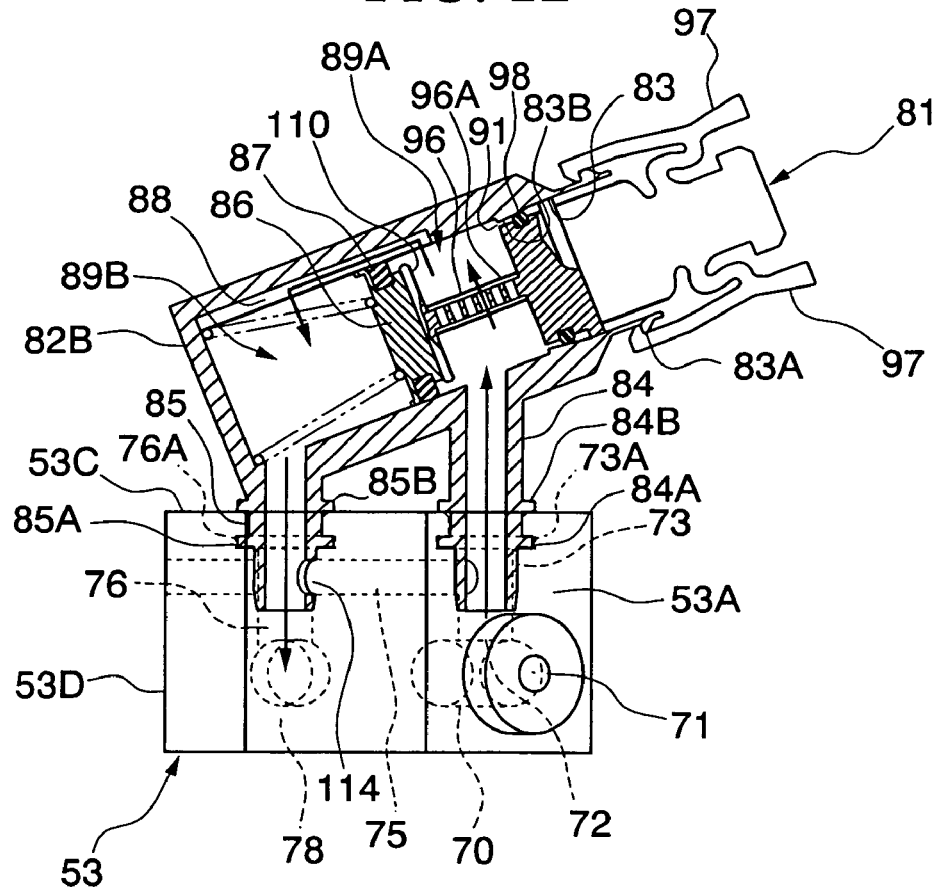
FIG. 12 is a sectional view showing the state of the tissue recovery device mounted on the attachment.

As shown in FIG. 12, by mounting the tissue recovery device 54 on the attachment 53, the distal end side conduit 84 is inserted into the first connection conduit 73. The distal end side conduit 84 advances toward the branch portion 72, passing the coupling position of the bypass conduit 75. The annular projection 84A becomes engaged in an annular groove 73A of the first connection conduit 73, and the annular projection 84B abuts the side surface 53C. Thereby, the first coupling conduit 70 becomes continuous with the space 89A of the tissue recovery device 54. Here, the filter portion 96 of the tissue recovery filter 81 is inserted. Similarly, the proximal end side conduit 85 is inserted into the second connection conduit 76, with the distal end portion thereof passing the bypass conduit 75. The annular projection 85A becomes engaged in an annular groove 76A, and the annular projection 85B abuts the side surface 53C. Thereby, the second coupling conduit 78 becomes continuous with the space 89B of the tissue recovery device 54.

Since the lid 86 is midway in the groove 88 of the case body 82, the first coupling conduit 70 and the second coupling conduit 78 are continuous via the groove 88 and the spaces 89A and 89B. Since the distal end side conduit 84 and the proximal end side conduit 85 are respectively inserted beyond the formation position of the bypass conduit 75, the bypass conduit 75 is closed off. Since the length of the distal end side conduit 84 is longer than the length of the proximal end side conduit 85, the tissue recovery device 54 is fixed in a state of being inclined so that the opening portion 83 is further from the attachment 53 than the bottom portion 82B.

Removing the tissue recovery device 54 from the attachment 53 opens up the bypass conduit 75. The distal end side connection port 74 and the proximal end side connection port 77 are thereby separately open to the outside.

Figure 13:
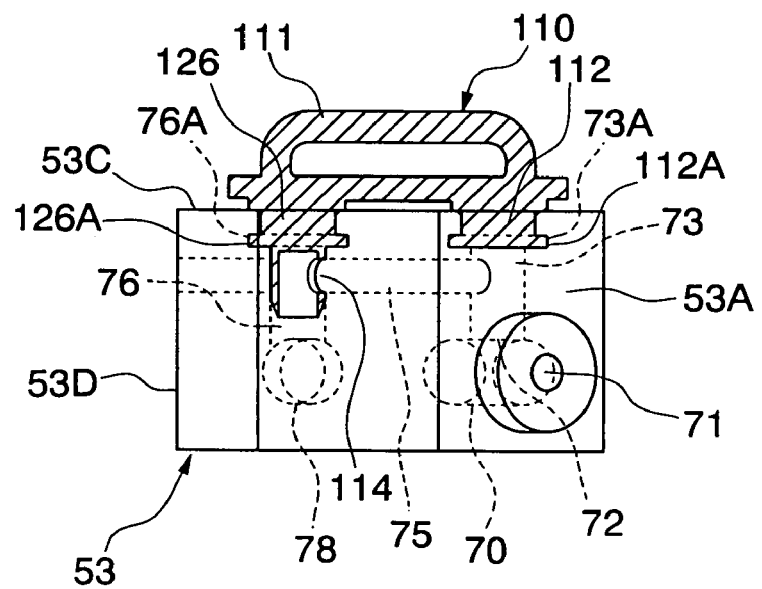
FIG. 13 is a drawing showing the state of plug bodies mounted on the attachment.

When the tissue recovery device 54 is removed from the attachment 53, a plug body 110 such as that shown in FIG. 13 is mounted in the attachment 53 to close the distal end side connection port 74, the proximal end side connection port 77, and the side surface 53D side of the bypass conduit 75 to the outside. The plug body 110 has a grip portion 111 to be grasped by the operator, a distal end side projection 112 (first plug body) that fits into the first connection conduit 73, and a proximal end side projection 126 (second plug body) that fits into the second connection conduit 76.

An annular projection 112A that engages with the annular groove 74A is provided on the outer circumference of the distal end side projection 112, and an annular projection 126A that engages with the annular groove 77A is provided on the outer circumference of the proximal end side projection 126. The distal end side projection 112 stops before the bypass conduit 75; but the proximal end side projection 126 advances beyond the bypass conduit 75 toward the second coupling conduit 78. The proximal end side projection 126 has a hollow shape and in a portion thereof a hole 114 that communicates with the bypass conduit 75 is formed. Accordingly, in the state of the plug body 110 mounted on the attachment 53, the first connection conduit 73 and the second connection conduit 76 are open for free passage via the bypass conduit 75. Note that the distal end side projection 112 and the proximal end projection 126 may also be two separate plug bodies.

The action of the embodiment shall be described.

As shown in FIG. 12, the tissue recovery device 54 is initially mounted on the attachment 53. Also, the first connection portion 68 and the second connection portion 69 of the endoscope operation portion 60 are fitted into the first coupling conduit 70 and the second coupling conduit 78 of the attachment 53, respectively, to fix the attachment 53 to the endoscope 52. At this time, as shown in FIG. 4, the attachment 53 is mounted with a side surface 53E (first surface) facing the endoscope operation portion 60. Thereby, the tissue recovery device 54 that is mounted on the side surface 53C (second surface) side is disposed on the side opposite the endoscope operation portion 60 in a state of sandwiching the attachment 53. In this state, the endoscope insertion portion 61 is inserted into a body, and the treatment tool (for example, resection forceps) is inserted from the treatment tool insertion port 71 of the attachment 53. The treatment tool is inserted from the first coupling conduit 70 of the attachment 53 into the working channel 65 on the endoscope 52 side to be projected from the distal end portion of the endoscope insertion portion 61. After tissue that is the sample object is resected by the treatment tool, the treatment tool is pulled out from the endoscope 52 and the attachment 53. The treatment tool insertion port 71 is hermetically closed by its own restoring force.

The suction unit 5 is activated when suctioning resected tissue. The suction force acts on the tissue through the suction conduit 66 (including the second coupling conduit 78 and the second connection conduit 76 of the attachment 53), the tissue recovery device 54, the first connection conduit 73, and the working channel 65 (including the first coupling conduit 70). As shown by the arrow in FIG. 3, the tissue travels with surrounding fluid from the working channel 65 to the branch portion 72, and from the branch portion 72, the tissue is guided to the first connection conduit 73 to be drawn into the space 89A of the tissue recovery device 54. The tissue becomes caught on the tissue trapping surface 96A of the filter portion 96 in the space 89A. The fluid passes through the mesh of the filter portion 96, is led from the groove 88 to the space 89B and, passing from the attachment 53 through the suction conduit 66, and is discharged from the suction unit 5. When the tissue is caught, the suction unit 5 is stopped. The tissue is recovered by removing the tissue recovery filter 81 from the tissue recovery case 80.

Since the opening portion 83 side in the longitudinal direction of the tissue recovery device 54 slopes in a direction away from the attachment 53, the tissue recovery filter 81 can be readily removed without interfering with the endoscope operating portion 60. In doing so, simply by pressing the pair of fixing portions 97 toward each other, the engagement with the tissue recovery case 80 is released. Therefore, the tissue recovery filter 81 can be removed with one hand. Also, since the opening portion 83 side in the vertical direction slopes upward, even in the case of fluid remaining in the case body 82, the fluid does not flow to the outside. When considerable fluid remains behind, the notches 101 in the plate 100 of the tissue recovery filter 81 ensure the fluid is not scooped out of the case body 82. When the tissue recovery filter 81 is removed, the biasing force of the coil spring 90 causes the lid 86 to rise until abutting the step portion 91 on the opening portion 83 side. As a result, the case body 82 is hermetically sealed by the sealing member 87 of the lid 86.

The present embodiment is constituted so that the tissue recovery device 54 is connected to the endoscope 52 via the attachment 53, which is used for insertion of the treatment tool. Therefore, the operator can readily operate the endoscope 52 without routing conduit for the tissue recovery device 54 to the outside. Since the tissue recovery device 54 is fixed in the vicinity of the endoscope operation portion 60, the operator can easily handle the tissue recovery device 54. Since the tissue recovery device 54 is attached at a position that does not interfere with the endoscope 52, operability is good. Since the tissue recovery device 54 slopes so that the opening portion 83 is upward, removal is simple and spillage of fluid that is inside is hindered. Since the tissue recovery filter 81 is clickably detachable with respect to the tissue recovery case 80, operations such as removal while holding the endoscope 52 becomes easy. Also, the operations of attaching and detaching the tissue recovery filter 81 several times to continuously retrieve tissue becomes easy. In the state of the tissue recovery filter 81 being removed, since the lid 86 hermetically seals the inside of the case body 82, the air tightness within the passages can be maintained.

The attachment 53 connects the tissue recovery device 54 to the conduit that branches off from the working channel 65 at the branch portion 72, therefore insertion and removal of the treatment tool becomes easy. In the state of the tissue recovery device 54 removed, mounting the plug body 110 (refer to FIG. 13) can maintain the air tightness of the conduit. Also, the working channel 65 and the suction conduit 66 can be brought into communicative connection through the bypass conduit 75. Since the bypass conduit 75 is opened to the side surface 53D, cleaning by inserting a cleaning brush is made easy. Since the attachment 53 is made of an elastic material, attachment to and detachment from the endoscope 2 is easy, and an airtight structure can be readily assembled. Also, since the attachment 53 is made of a comparatively flexible material compared to the endoscope 2, abrasion hardly occurs on the endoscope 2 even with repeated attachment and detachment. For this reason, the cost of the endoscope system 1 as a whole can be decreased.

Modification examples of the present embodiment shall be described below.

Figure 14:
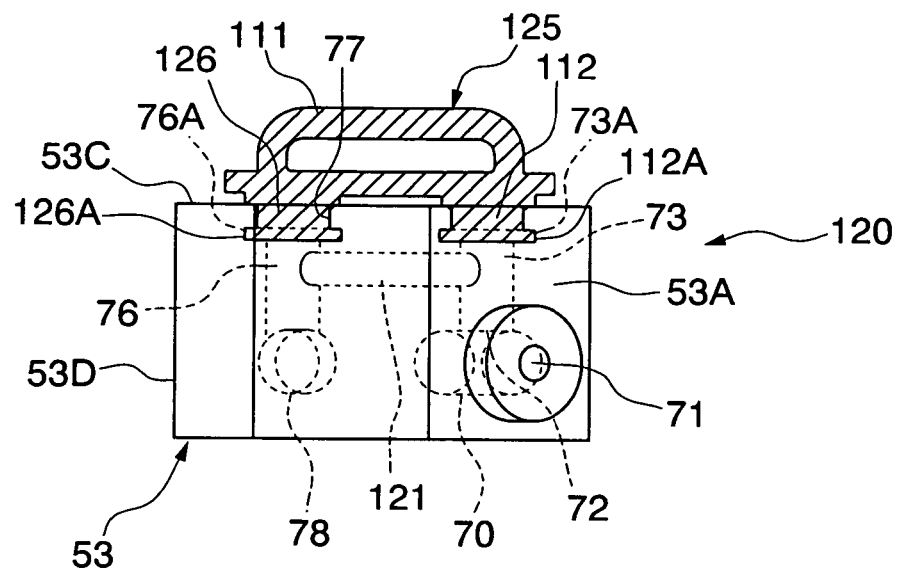
FIG. 14 is a drawing showing the plug body in the attachment in which a bypass conduit is not opened to the side surface.

An attachment 120 shown in FIG. 14 has a bypass conduit 121 that does not open to the side surface 53D. A plug body 125 that is applied to the attachment 120 has the grip portion 111, the distal end side projection 112 (first plug body), and the proximal end side projection 126 (second plug body). The length of the proximal end side projection 126 is shorter than the length from the proximal end side connection port 77 to the merging position of the bypass conduit 121. The proximal end side projection 126 is engaged in the second connection conduit 76 by the annular projection 126A. The working channel 65 is brought into communicative connection with the suction conduit 66 via the first connection conduit 73, bypass conduit 121, and the second connection conduit 76.

Figure 15:
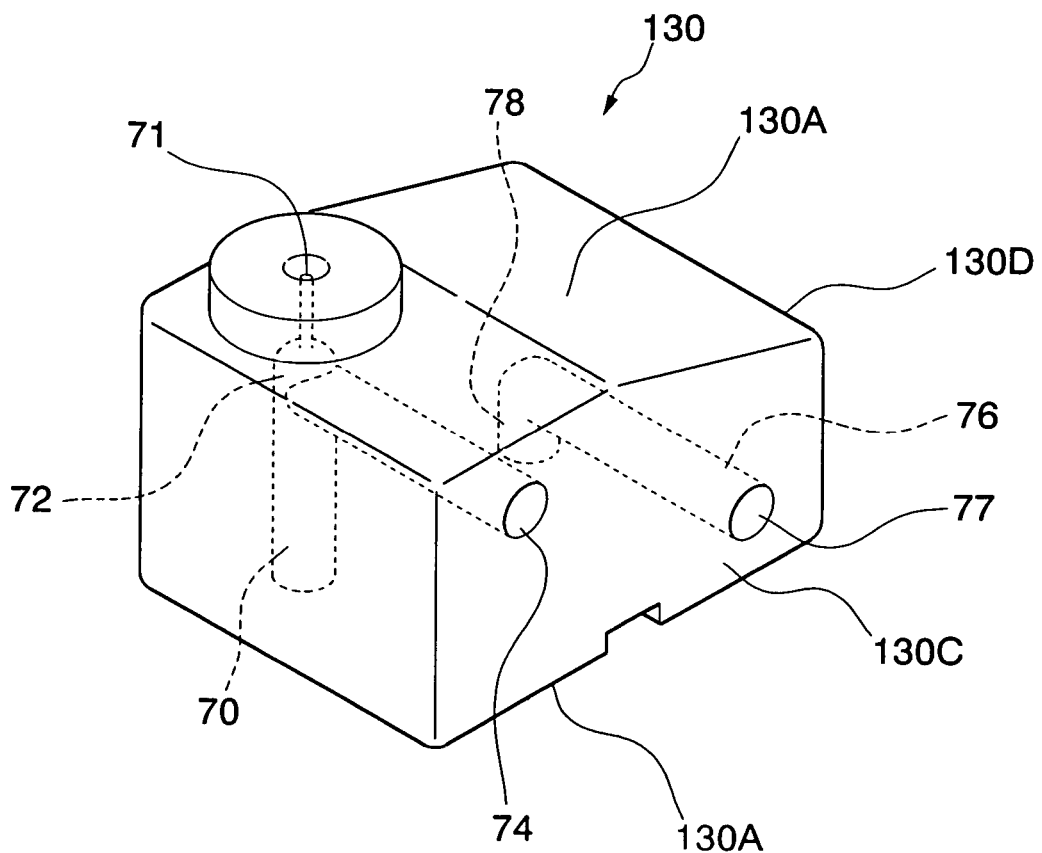
FIG. 15 is a perspective drawing of the attachment that does not have a bypass conduit.
Figure 16:
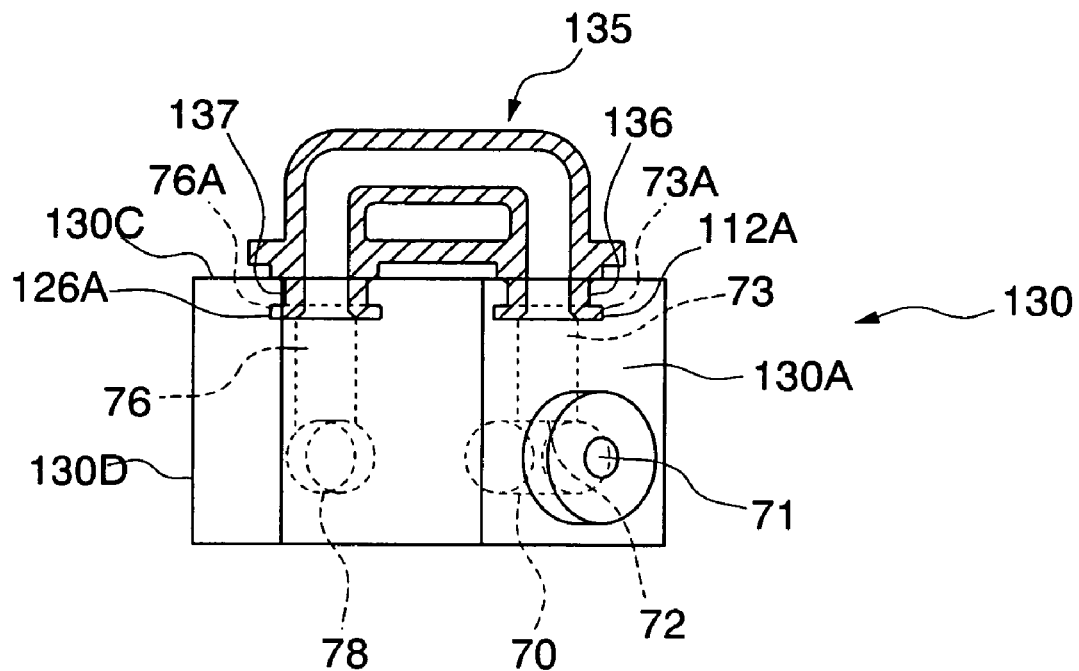
FIG. 16 is a drawing showing the constitution of a plug body with respect to the attachment shown in FIG. 15.

An attachment 130 shown in FIG. 15 and FIG. 16 does not have a bypass conduit. When the tissue recovery device 54 is removed, a coupling pipe 135 (coupling member) is mounted. The coupling pipe 135 consists of a distal end side connection portion 136 and a proximal end side connection portion 137 at each end, respectively. The distal end side connection portion 136 is fitted into the first connection conduit 73, and the proximal end side connection portion 137 is fitted into the second connection conduit 76. This coupling pipe 135 is made from a plastic or elastic member. When the coupling pipe 135 is mounted, the distal end side connection port 74 and the proximal end side connection port 77 are hermetically sealed with respect to the outside, and so the working channel 65 is brought into communicative connection with the suction conduit 66 via the first connection conduit 73, the coupling pipe 135, and the second connection conduit 76.

Figure 17:
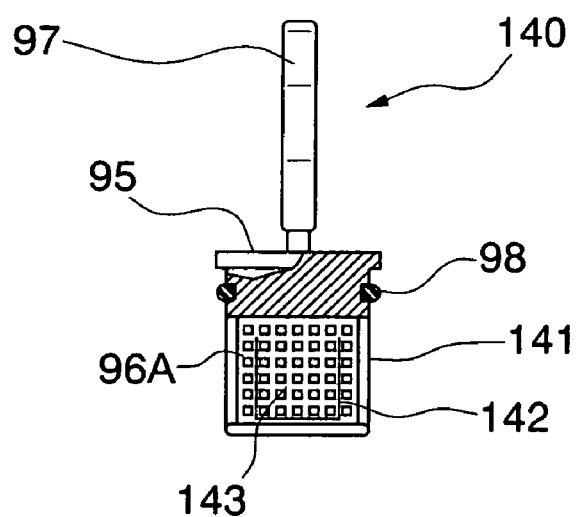
FIG. 17 is a drawing showing the tissue recovery filter having a movable portion.
Figure 18:
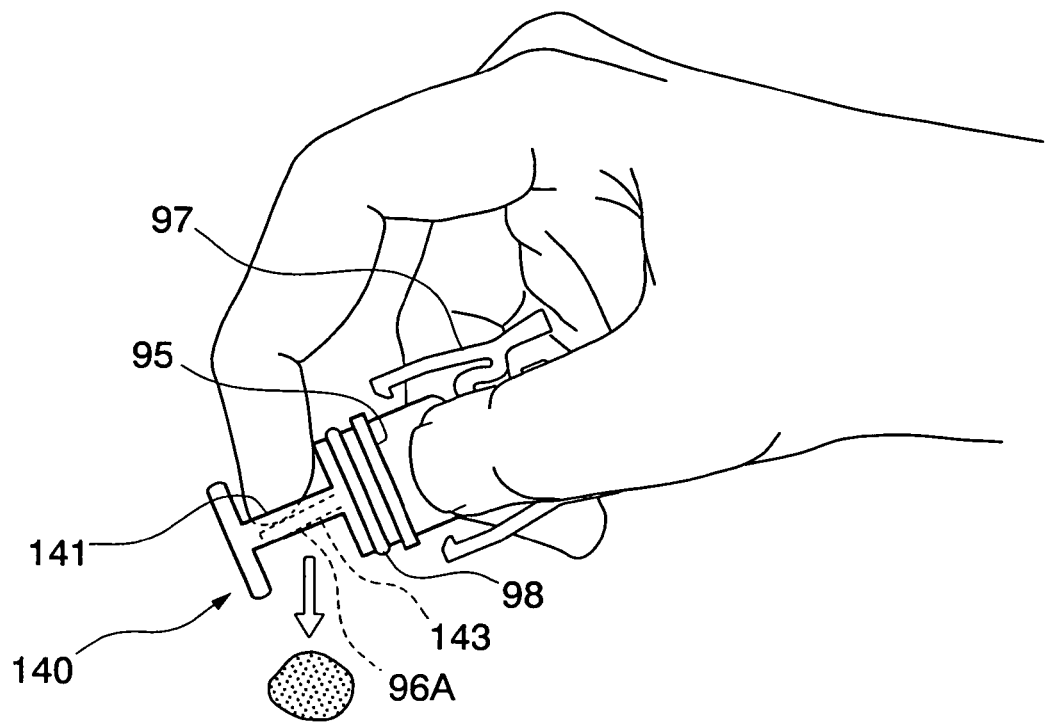
FIG. 18 is an explanatory drawing of the operation of removing tissue by pressing the movable portion with a finger.
Figure 19:
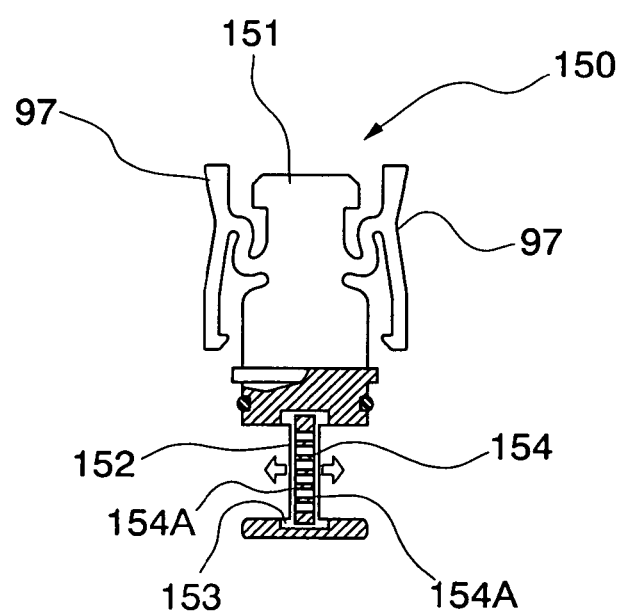
FIG. 19 is a partial cutaway view showing the constitution of a tissue recovery filter in which the movable portion is constituted from a separate body.

A tissue recovery filter 140 shown in FIG. 17 has a filter portion 141 in which a U-shaped slit 142 is formed. The slit 142 is formed within the tissue trapping surface 96A, which is vertical to the mesh, so that the region surrounded by the slit 142 becomes a movable portion 143. As shown in FIG. 18, by using a finger to press the movable portion 143 in the state of having trapped a tissue, the trapped tissue can readily fall away. FIG. 19 shows another embodiment of the moving portion 143. Here, a tissue recovery filter 150 has a frame 152 provided in an extending manner from a main body 151. A groove 153 is formed along the inner periphery of the frame 152, with a movable portion 154 inserted therein. The movable portion 154 has a mesh structure, with a tissue trapping surface 154A provided on the front face and back face through which fluid is allowed to pass but tissue is caught. Since the groove 153 provides play with respect to the external dimensions of the movable portion 154, the tissue can be made to separate by moving the movable portion 154 by hand.

Figure 20:
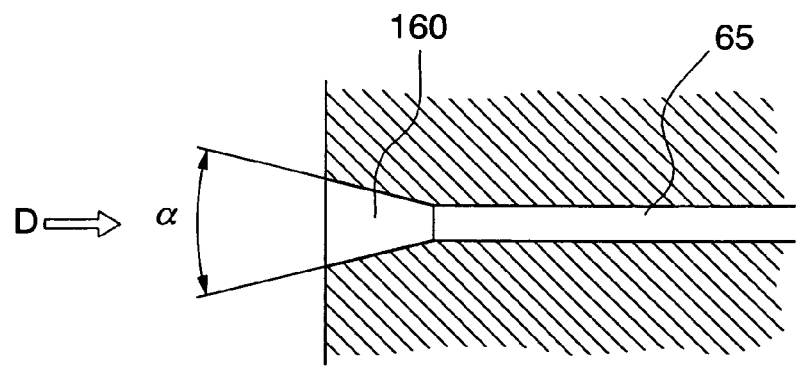
FIG. 20 is a sectional view of the distal end portion of the endoscope insertion portion showing the shape of the distal end portion of the working channel.
Figure 21:
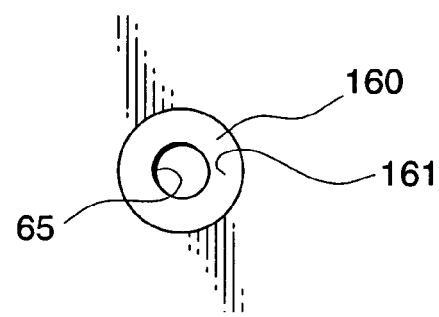
FIG. 21 is a view from arrow D in FIG. 20.
Figure 22:
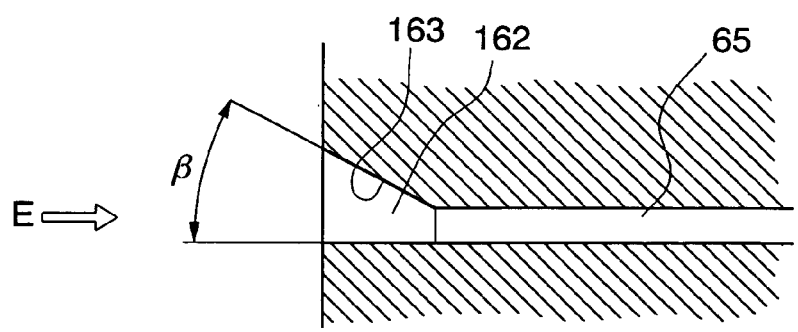
FIG. 22 is a sectional view of the distal end portion of the endoscope insertion portion showing the shape of the distal end portion of the working channel.
Figure 23:
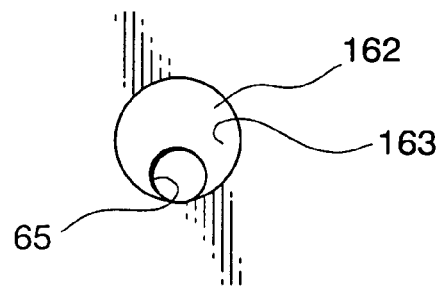
FIG. 23 is a view from arrow E in FIG. 22.

Also, a distal end opening portion of the working channel 65 as shown from FIG. 20 to FIG. 23 may be used. A distal end opening portion 160 of the working channel 65 shown in FIG. 20 and FIG. 21 is formed from a tapered surface 161 that has an inclination angle of angle α with respect to the outer diameter of the working channel 65 so that the distal end side has an expanded diameter. Here, the inclination angle α is an angle greater than 0 degrees and not greater than 5 degrees. When 0 degree, tissue may be hindered from entering the working channel 65 in the case the tissue being comparatively large. When greater than 5 degrees, tissue easily becomes clogged on the tapered surface 161. A distal end opening portion 162 shown in FIG. 22 and FIG. 23 has a tapered surface 163 of inclination angle β. The tapered surface 163 is eccentric with respect to the axial line of the working channel 65. The inclination angle β is greater than 0 degrees and not greater than 5 degrees. The reasons therefor, and the action of the distal end opening portion 162 are the same as for the embodiment shown in FIG. 20.

Third Embodiment

A third embodiment of the present invention will be described with reference to FIGS. 24 through 29. The third embodiment shows a modification example of the attachment and the tissue recovery device. Constituent elements similar to those in the aforedescribed embodiments will be given the same reference numerals and explanations thereof will be omitted here.

Figure 24:
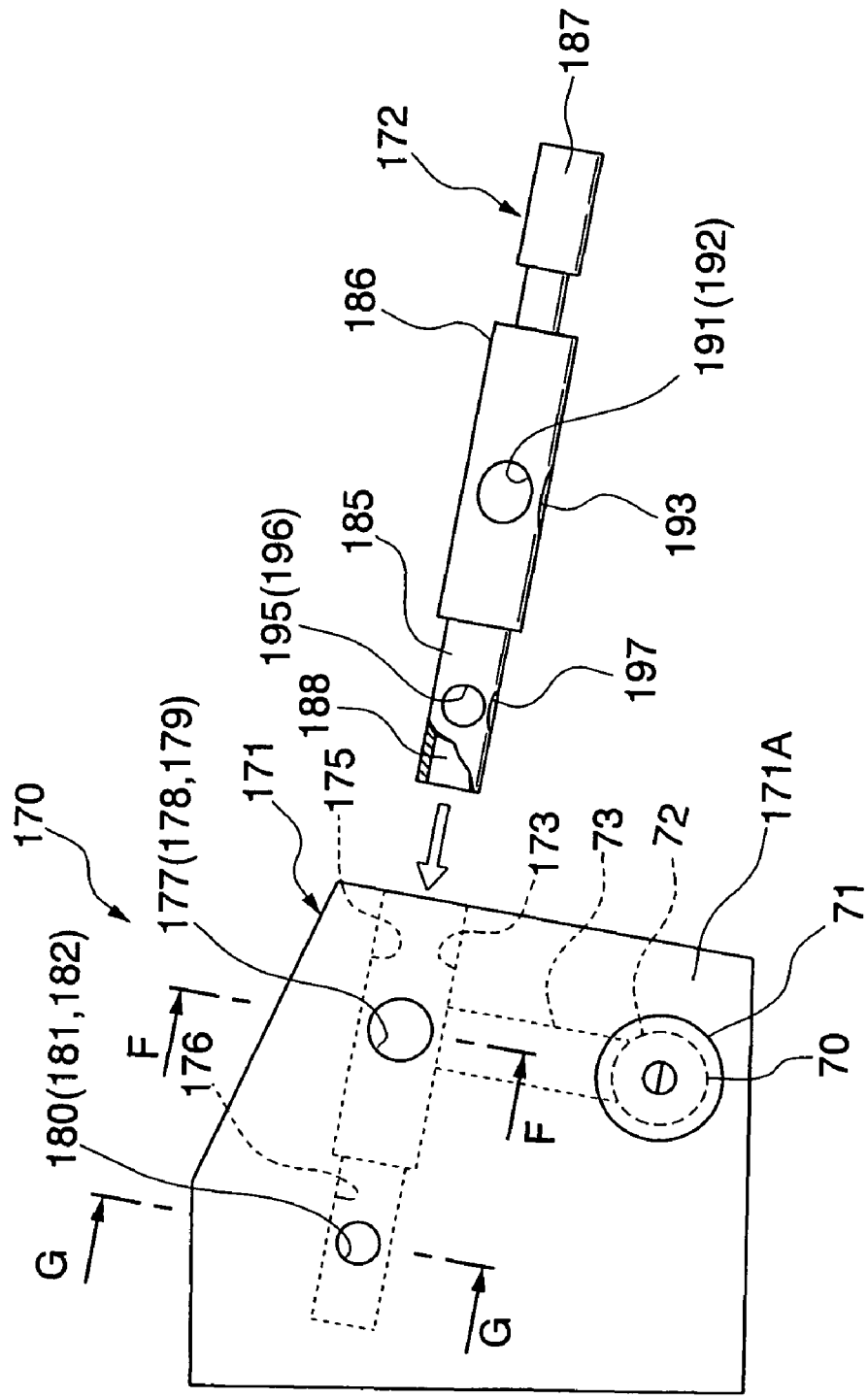
FIG. 24 is a plan view showing the constitution of the attachment having a valve.
Figure 25:
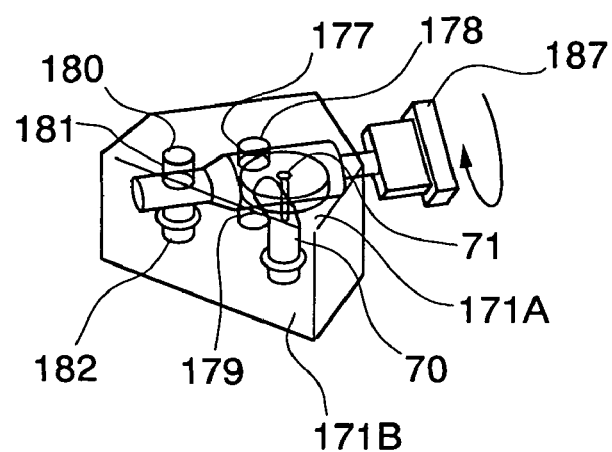
FIG. 25 is a perspective view of the attachment shown in FIG. 24.

As shown in FIG. 24, an attachment 170 has a body portion 171 and a valve 172 that is inserted in the body portion 171 to rotate freely. The body portion 171 has the first coupling conduit 70. The treatment tool insertion port 71 that opens to a top surface 171A is provided in the first coupling conduit 70, and the first connection conduit 73 branches off from the branch portion 72. The first connection conduit 73 is in communicative connection with an insertion hole 173 in which the valve 172 is inserted. The insertion hole 173 has a large diameter portion 175 and a small diameter portion 176. The first connection conduit 73 opens to the large diameter portion 175 of the insertion hole 173 in the body portion 171. Moreover, a hole 177 is formed at a position that is rotated approximately 90 degrees in the circumferential direction from the connection location of the first connection conduit 73. The hole 177 opens to the top surface 171A and extends beyond the insertion hole 173 toward the bottom surface 171B, but does not pierce the bottom surface 171. The upper side of the hole 177 from the insertion hole 173 serves as a distal end side opening portion 178, and the lower side of the hole 177 from the insertion hole 173 serves as an interposition hole 179. A through hole 180 is formed in the small diameter portion 176 of the insertion hole 173. The top surface 171A side of the through hole 180 beyond the insertion hole 173 serves as a proximal end side connection port 181. The bottom surface 171B side of the insertion hole 173 serves as a second coupling conduit 182.

The valve 172 is inserted in the insertion hole 173 and rotates freely around its axis while maintaining airtightness. The valve 172 has a distal end portion 185 with a narrow diameter and a proximal end portion 186 with a large diameter. A knob 187 for the operator to rotate the valve 172 is provided at the proximal end portion 186. A bypass conduit 188 is formed in the valve 172. The proximal end portion 186 side of the bypass conduit 188 is closed off.

Figure 26:
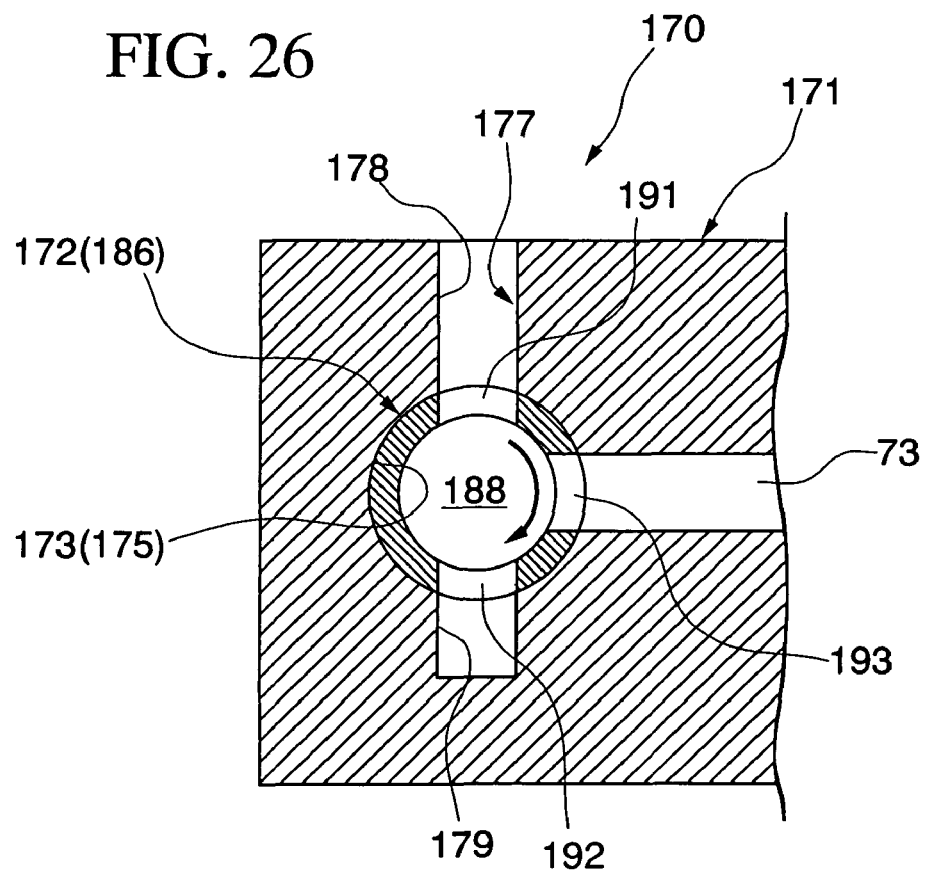
FIG. 26 is a sectional view along line F-F in FIG. 24.

The proximal end portion 186 of the valve 172 has two through holes 191 and 192 formed on the same axis and a through hole 193 that is formed at a position perpendicularly intersecting these through holes 191 and 192. When the valve 172 is inserted in the body portion 171 in the rotation position (first rotation position) shown in FIG. 24, as shown in FIG. 26 the through hole 191 is brought into communicative connection with the distal end side opening portion 178 and the bypass conduit 188, and the through hole 192 is brought into communicative connection with the interposition hole 179 and the bypass conduit 188. The through hole 193 brings the first connection conduit 73 and the bypass conduit 188 into communicative connection. In a position rotated 90 degrees clockwise in the direction of the arrow from the rotation position as shown in FIG. 26 (that is, in the second rotation position), the through hole 191 links with the first connection conduit 73, and the through hole 193 links with the interposition hole 179. The through hole 192 is thereby closed off.

Figure 27:
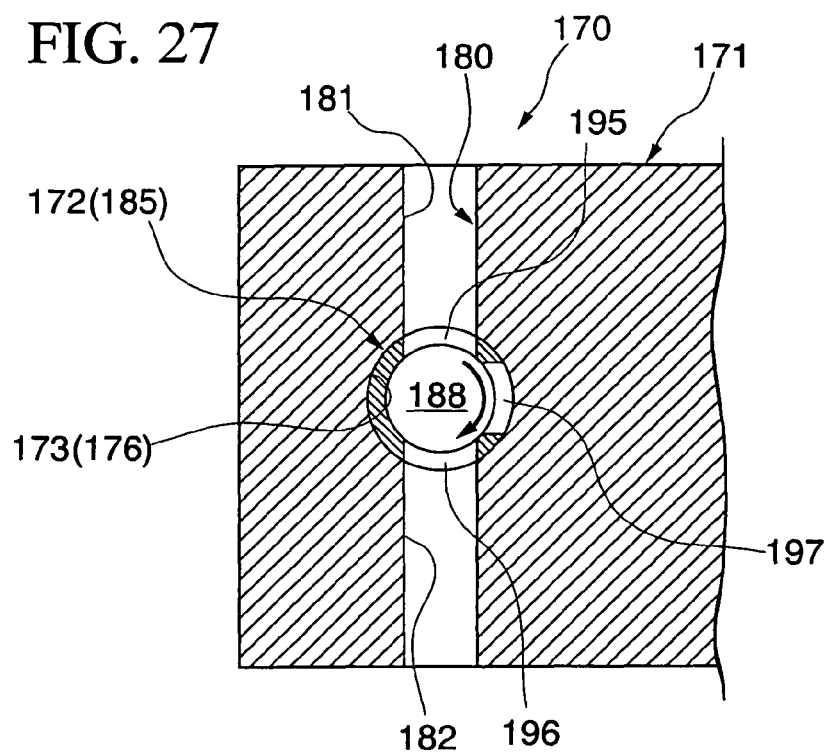
FIG. 27 is a sectional view along line G-G in FIG. 24.

Similarly, the distal end portion 185 of the valve 172 shown in FIG. 24 has two through holes 195 and 196 that are formed on the same axis and a through hole 197 that is formed at a position perpendicularly intersecting these through holes 195 and 196. When the valve 172 is inserted in the body portion 171 in the first rotation position shown in FIG. 24, as shown in FIG. 27, the through hole 195 is brought into communicative connection with the proximal end side connection port 181 and the bypass conduit 188, and the through hole 196 is brought into communicative connection with the second coupling conduit 182 and the bypass conduit 188. The through hole 197 is closed off by the body portion 171. In the second rotation position rotated 90 degrees clockwise in the direction of the arrow from the rotation position shown in FIG. 26, the through hole 195 and the through hole 196 are closed off by the body portion 171, and the through hole 197 links with the second coupling conduit 182.

Figure 28:
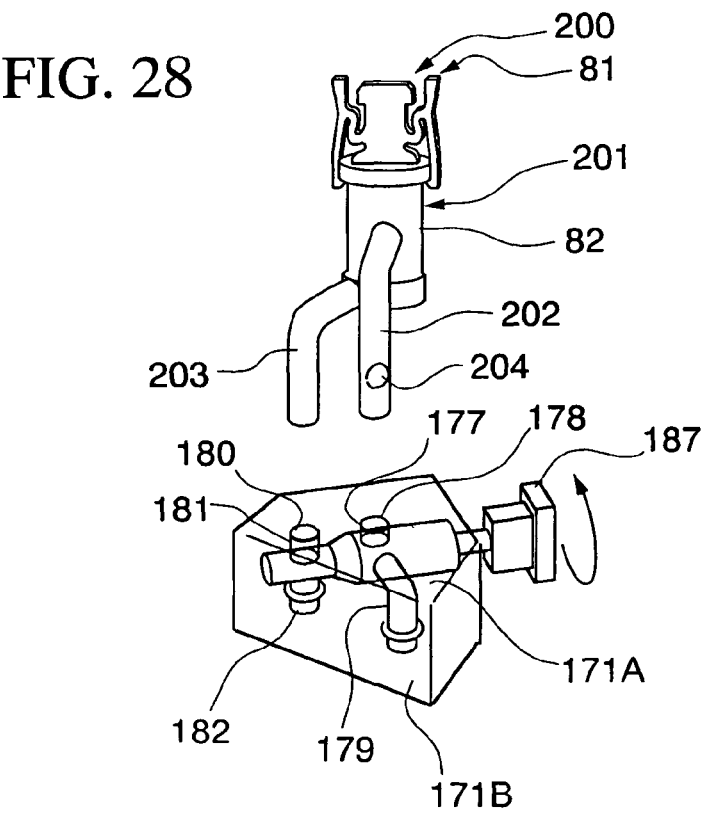
FIG. 28 is a perspective view showing the attachment and the tissue recovery device.

FIG. 28 shows a tissue recovery device 200 that is used together with the attachment 170. The tissue recovery device 200 has a tissue recovery case 201 and a tissue recovery filter 81. The tissue recovery case 201 is provided with a distal end side conduit 202 and a proximal end side conduit 203 that are disposed at a specified interval in the axial direction from the case body 82. Other constitution of the tissue recovery case 201 is the same as the constitution of the second embodiment. The distal end side conduit 202 and the proximal end side conduit 203 are each bent and then extend in a parallel manner. A connection conduit 204 that brings the inside and outside into communicative connection at a specified location is formed on the side portion of the distal end side conduit 202.

When the tissue recovery device 200 is not mounted, the valve 172 is set in the second rotation position.

The first coupling conduit 70 is coupled to the second coupling conduit 182 through the bypass conduit 188 of the valve 172. Since the other through holes 192, 193, 195, and 196 of the valve 172 are closed off by the body portion 171, the working channel 65 and the suction conduit 66 are brought into communicative connection while maintaining airtightness with the outside.

Figure 29:
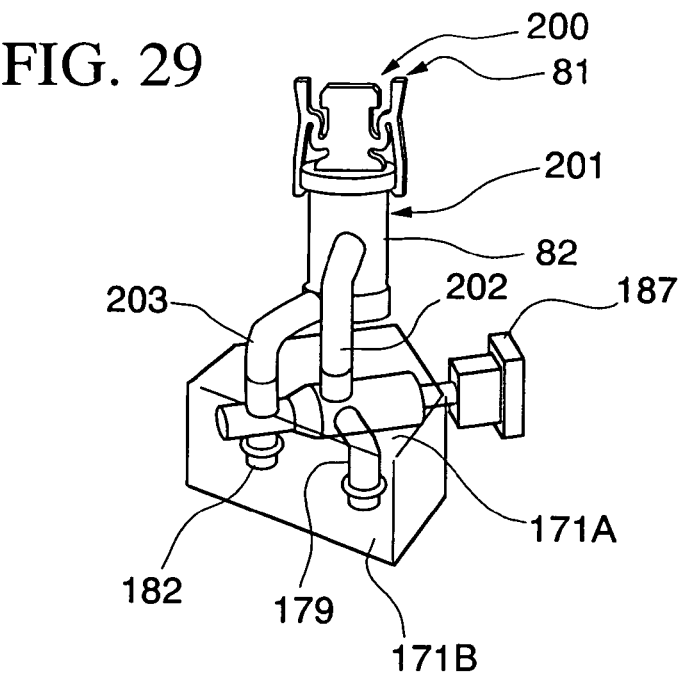
FIG. 29 is a perspective view showing the state of the tissue recovery device mounted on the attachment.

As shown in FIG. 29, when mounting the tissue recovery device 200 on the attachment 170, the valve 172 is set to the first rotation position. The distal end side conduit 202 is inserted into the distal end side opening portion 178, penetrating the valve 172 to be fit into the interposition hole 179. At this time, the connection conduit 204 of the distal end side conduit 202 and the first connection conduit 73 are brought into communicative connection. The proximal end side conduit 203 is inserted into the proximal end side connection port 181, penetrating the valve 172 to be fit into the second coupling conduit 182.

Since an airtight structure is formed by the proximal end side connection port 181 and the second coupling conduit 182, the bypass conduit 188 is closed off, and the first coupling conduit 70 and the second coupling conduit 182 are brought into communicative connection by the conduit that passes through the tissue recovery device 200.

When using the attachment 170 and the tissue recovery device 200 to recover tissue, the attachment 170 is mounted on the endoscope 52. The working channel 65 (including the first coupling conduit 70) and the suction conduit 66 (including the second coupling conduit 182) are brought into communicative connection via the tissue recovery device 200. This operation thereafter is carried out similarly to the second embodiment. The tissue passes from the working channel 65, traveling through the branch portion 72, to go along the first connection conduit 73 and the distal end side conduit 202 to be caught on the filter portion 96 (refer to FIG. 8). The fluid is discharged from the proximal end side conduit 203 and suctioned to the suction conduit 66.

According to the present embodiment, the tissue recovery device 200 is connected to the endoscope 52 via the attachment 170, which is used for insertion of the treatment tool. Therefore, the operator can readily operate the endoscope 52 without conduit for the tissue recovery device 200 being routed to the outside. Since the tissue recovery device 200 is fixed in the vicinity of the endoscope operation portion 60, handling by the operator of the tissue recovery device 200 becomes easy.

When removing the tissue recovery device 200, rotation of the valve 172 can seal off the conduit to the outside even without mounting a separate plug body. Moreover, the working channel 65 and the suction conduit 66 can be brought into communicative connection via the bypass conduit 188. Accordingly, it is possible to simplify the operation when the tissue recovery device 200 is removed.

The present invention can be widely applied without being limited to the aforedescribed embodiments.

For example, the tissue recovery device may have any constitution that is mountable on the endoscope 2 or the attachment 53 and 170, without being limited to the constitution of the tissue recovery device 3, 54, 200 of the aforedescribed embodiments.

FIGS. 30 to 33 show examples of another attachment and tissue recovery device that can solve problems similar to the present invention.

Figure 30:
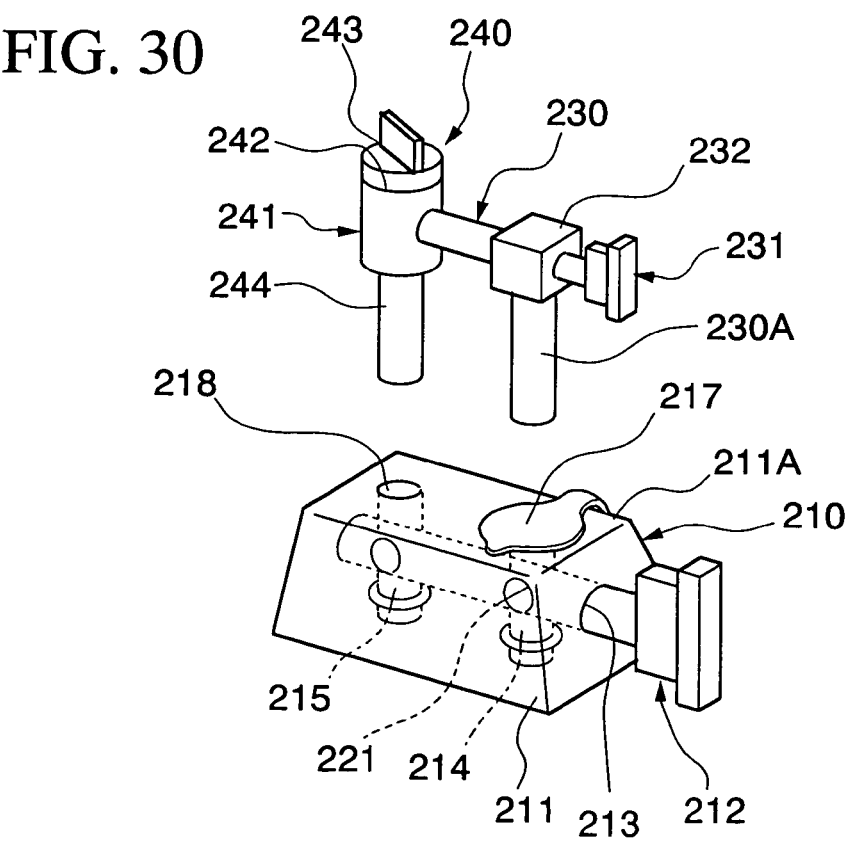
FIG. 30 is a perspective view showing the attachment and the tissue recovery device.
Figure 31:
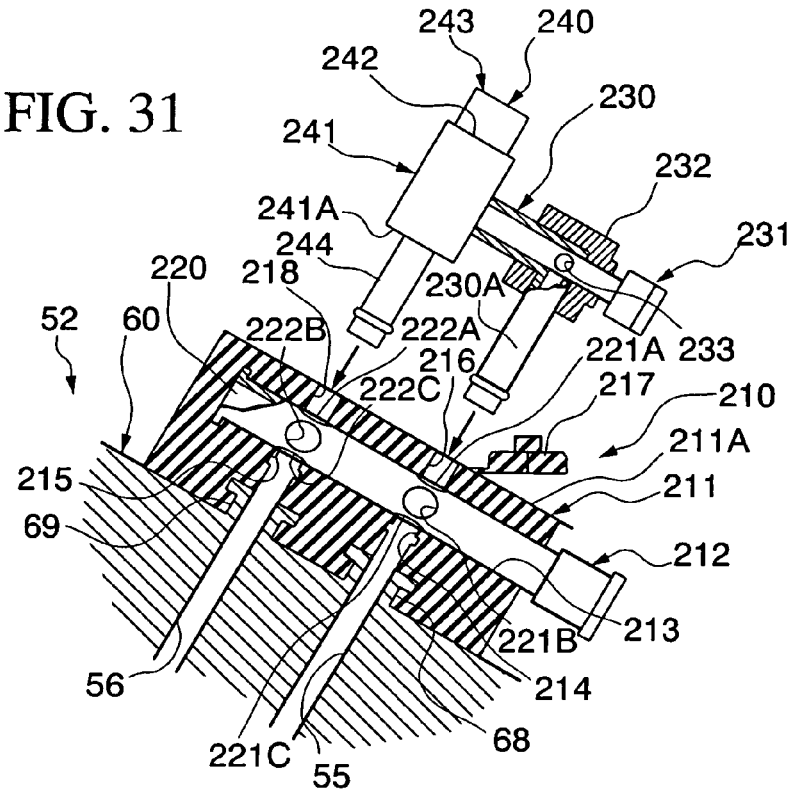
FIG. 31 is a sectional view showing the attachment and the tissue recovery device.

In an attachment 210 shown in FIG. 30 and FIG. 31, a valve 212 is inserted in a body 211 to rotate freely. A first coupling conduit 214 and a second coupling conduit 215 pass through the body portion 211 in parallel so as to go through an insertion hole 213 in which the valve 212 is to be inserted. A forceps plug lid 217 is detachably provided on a distal end opening portion 216 of the first coupling conduit 214 that opens to a top surface 211A of the body portion 211. Also, the opening of the second coupling conduit 215 on the top surface 211A becomes a proximal end side connection port 218. The valve 212 is inserted in the insertion hole 213 to rotate freely while maintaining the airtightness. A bypass conduit 220 is formed inside of the valve 212. At the proximal end side of the valve 212, four through holes 221A, 221B, 221C, and 221D are formed at a regular interval in the circumferential direction of the valve 212 at a position corresponding to the first coupling conduit 214. Also, at the distal end side of the valve 212, three through holes 222A, 222B, and 222C are formed at a position corresponding to the second coupling conduit 215. The through hole 222A and the through hole 222C are disposed on the same shaft line, and the through hole 222B is formed at a position shifted by 90 degrees from the two through holes 222A and 222C.

Figure 32:
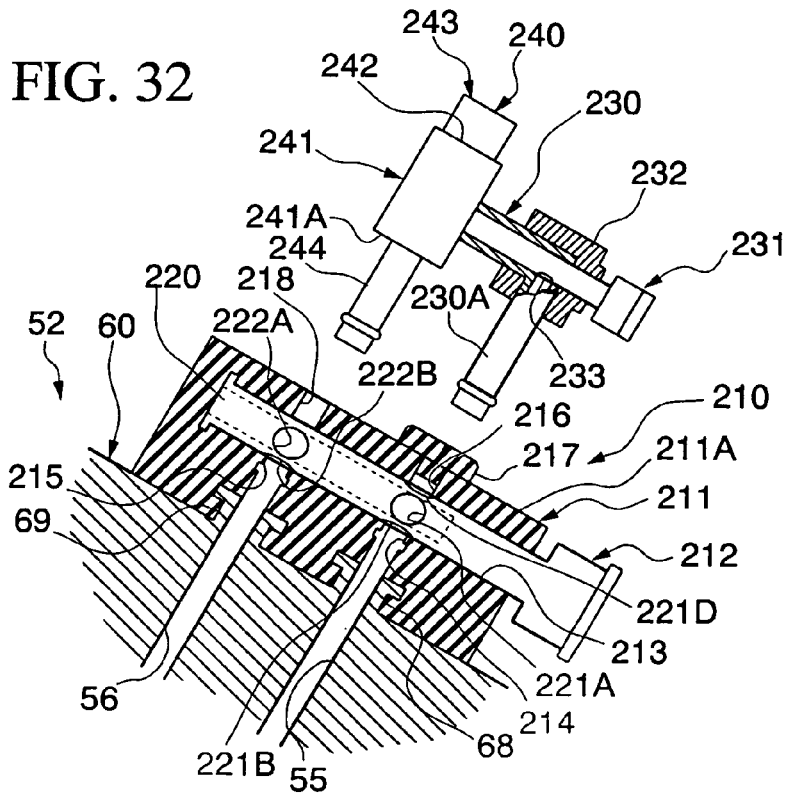
FIG. 32 is a drawing showing the state of the valve rotated to the second position.
Figure 33:
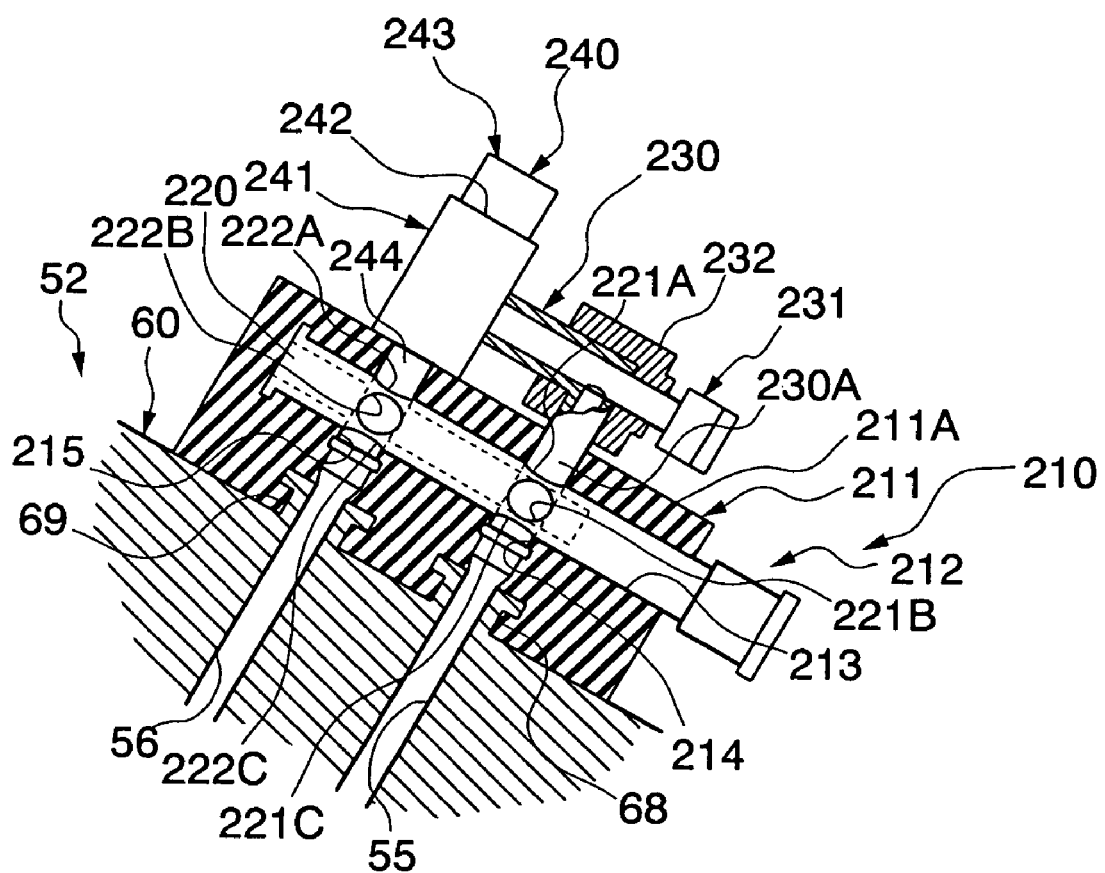
FIG. 33 is a drawing showing the state of the tissue recovery device mounted.

As shown in FIG. 32, when the valve 212 is in the first rotation position, the first coupling conduit 214 and the bypass conduit 220 are connected by the through hole 221B. At the second coupling conduit 215, only the suction conduit 66 is connected to the bypass conduit 220 by the through hole 222B. As a result, the working channel 65 and the suction conduit 66 are coupled via the bypass conduit 220. The remaining through holes 222A and 222C are closed off by the body portion 211. In this case, when the forceps plug lid 217 is mounted, the distal end opening portion 216 and the through holes 221 are isolated from the outside. When the forceps plug lid 217 is removed, it is possible to insert a treatment tool such as forceps. As shown in FIG. 31, in the second rotation position, the first coupling conduit 214 and the second coupling conduit 215 are respectively opened for passage, and the first coupling conduit 214 and the second coupling conduit 215 are brought into communicative connection via the bypass conduit 220. Here, as shown in FIG. 33, when the tissue recovery device 240 that is provided with a connection conduit 230 is mounted, the working channel 65 and the suction conduit 66 are connected by the internal conduit in the tissue recovery device 240, and the bypass conduit 220 is closed off. Here, the tissue recovery device 240 has a tissue recovery case 241 and a tissue recovery filter 243 that is inserted from an opening portion 242 of the tissue recovery case 241, with a proximal end side conduit 244 is provided at the bottom portion 241A of the tissue recovery case 241. A connection conduit 230 is connected to the side portion of the tissue recovery case 241. The connection conduit 230 bends in an L shape and is continuous with the inside of the tissue recovery case 241. A valve 231 is inserted to rotate freely in the angle portion of the connection conduit 230. The valve 231 is mounted to rotate freely on a support portion 232 made of rubber that covers the angle portion of the connection conduit 230, and air tightness is maintained with respect to the outside. The valve portion 231 is hollow, and a through hole 233 is formed at one location. By aligning the through hole 233 with a conduit 230A on the insertion side of the connection conduit 230, the connection conduit 230 becomes continuous so that tissue can be recovered. By rotating the valve 231 to shift the position of the through hole 233, the connection conduit 230 is closed off.

When the suction unit 5 (refer to FIG. 3) is activated in the state of the tissue recovery device 240 being mounted, tissue is drawn from the working channel 65 through the connection conduit 230 to be led to the tissue recovery device 240, where it is trapped on the filter portion having a constitution identical to that shown in FIG. 8. The fluid is discharged from the proximal end side conduit 244 to pass through the suction conduit 66.

The constitution of this endoscope system is such that the tissue recovery device is provided in the endoscope operating portion and a conduit that joins the endoscope and the tissue recovery device is not drawn to outside the endoscope. Tissue passes from the distal end portion of the endoscope insertion portion through the branch portion to be recovered in the tissue recovery device. Also, the tissue recovery device is disposed in the conduit after the branch off from the working channel. When passing a treatment tool through the endoscope, it passes from the working channel through the branch portion to be projected from the distal end portion of the suction conduit, so that the treatment tool does not interfere with the tissue recovery device.

This endoscope system provides the branch portion in the working channel and recovers tissue in the tissue recovery device along a conduit that branches off from the branch portion. Fluid that is suctioned together with tissue is discharged from the tissue recovery device to pass through the suction conduit in the endoscope. For this reason, a conduit that is used solely for exhaust to outside the endoscope is not routed. Also, since the tissue recovery device is disposed in the conduit that has branches off from the working channel, the treatment tool does not interfere with the tissue recovery device.

In this endoscope system, the tissue recovery device is connected to the endoscope via the attachment. The suction operation can therefore be performed without routing a conduit for the tissue recovery device to outside the endoscope. In this endoscope system, the tissue recovery device can be removed from the attachment to be separately handled. This is convenient when continuously sampling tissue several times and when cleaning after use.

In this endoscope system, the attachment can be easily installed on the endoscope. Also, since the durability of the attachment is relatively lower than the endoscope, the cost of the entire endoscope system can be reduced.

In this endoscope system, when the tissue recovery device is not used, the working channel side and the suction conduit communicate through the bypass conduit.

This endoscope system can recover tissue by removing only the tissue recovery filter in the state of the tissue recovery case being attached to the endoscope side. When continuously sampling tissue several times, attachment and detachment of the tissue recovery filter can be repeated each time tissue is suctioned.

In this endoscope system, turning the valve can selectively switch between a conduit system that performs suction through the tissue recovery device and a conduit system that causes the suction conduit to directly communicate with the working channel through the bypass conduit.

In this endoscope system, simply by mounting the tissue recovery filter on the tissue recovery case, tissue recovery can be carried out regardless of the orientation of the tissue recovery filter.

In this endoscope system, when the coupling member is mounted, the working channel and the suction conduit are connected through the conduit of the coupling member.

In this endoscope system, when the tissue recovery device is removed, the two plug bodies are fitted to tightly seal the openings of the conduits. In the case of the plug bodies having a shape that does not block the bypass conduit, the working channel and the suction conduit are allowed to communicate through the bypass conduit.

In this endoscope system, since the tissue recovery device is disposed on the opposite side of the endoscope viewed from the attachment, the operator can easily handle the tissue recovery device.

In this endoscope system, the tissue recovery device can be handled separately by being removed from the suction conduit, that is, the endoscope. This is convenient when sampling tissue several times and when cleaning after use.

According to the present invention, because there is no need to separately draw a conduit for suctioning and recovering tissues outside the endoscope, the burden on the operator when operating the endoscope system can be reduced and the procedure becomes easier. Because the conduit is branched at the branch portion and the treatment tool is inserted from one of the branched conduits and the tissue is guided to the tissue recovery device through the other conduit, the tissue recovery device does not interfere when the treatment tool is inserted to or from the conduit and the procedure by the operator can be performed effectively.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope system comprising:
   an endoscope in which an endoscope insertion portion that is inserted into a body extends from an endoscope operation portion that an operator controls;
   a working channel that opens to a distal end portion of the endoscope insertion portion and passes through the endoscope, with its proximal end portion opening to the endoscope operation portion;
   a connection conduit that branches from a branch portion formed in the proximal end portion of the working channel;
   a suction conduit for suctioning tissue, being connected to a suction unit through the inside of the endoscope;
   a tissue recovery device that is inserted into the connection conduit and a distal end of the suction conduit and is capable of trapping tissue which is drawn into the working channel by a suction of the suction unit via the suction conduit; and
   an attachment that removably attaches a portion of the working channel that includes the branch portion and the distal end portion of the suction conduit with respect to the endoscope operation portion as one piece, wherein the attachment has a bypass conduit that bypasses the tissue recovery device to allow communication between the connection conduit and the suction conduit, with the bypass conduit being blocked when the tissue recovery device is attached and opened when the tissue recovery device is removed.

2. The endoscope system according to claim 1, wherein the tissue recovery device is removably attached to the attachment.

3. The endoscope system according to claim 2, wherein the attachment has a main body portion that is attached to and detached from the endoscope and a valve that is inserted to rotate freely in the main body, with the valve being rotated so as to be able to select a first rotation position that allows communication between the distal end portion of the suction conduit and the proximal end portion of the working channel via the bypass conduit, and a second rotation position that blocks the bypass conduit to separately open the distal end of the suction conduit and the proximal end portion of the working channel to the outside.

4. The endoscope system according to claim 2, further comprising a coupling member that is mountable on a distal end side connection port that is provided on a proximal end of the connection conduit of the attachment to be connectable with the tissue recovery device and a proximal end side connection port that is provided on the conduit forming the distal end of the suction conduit in the attachment to be connectable with the tissue recovery device to fluidly connect the working channel and the suction conduit.

5. The endoscope system according to claim 1, wherein the attachment is manufactured from an elastic member.

6. The endoscope system according to claim 1, wherein the tissue recovery device has a tissue recovery case and a tissue recovery filter that is removably attached to the tissue recovery case.

7. The endoscope system according to claim 6, wherein the tissue recovery filter consists of two tissue trapping surfaces provided back to back, and the tissue recovery case is constituted so as to mount the tissue recovery filter so that the tissue trapping surfaces are disposed approximately perpendicular to a flow path of a fluid that suctions tissue.

8. The endoscope system according to claim 4, provided with a first plug body that is mountable in the distal end side connection port of the connection conduit that is open to the outside when the tissue recovery device is removed from the attachment, and a second plug body that is mountable in the distal end side connection port of the connection conduit that is open to the outside when the tissue recovery device is removed from the attachment.

9. The endoscope system according to claim 1, wherein the attachment has a first face that faces the endoscope operation portion when mounted on the endoscope operation portion and is constituted so that the tissue recovery device is disposed on a second face that is on an opposite side of the first face.

* * * * *